US011412917B2

(12) United States Patent
Oosake

(10) Patent No.: US 11,412,917 B2
(45) Date of Patent: Aug. 16, 2022

(54) MEDICAL IMAGE PROCESSOR, ENDOSCOPE SYSTEM, AND METHOD OF OPERATING MEDICAL IMAGE PROCESSOR

(71) Applicant: FUJIFILM Corporation, Tokyo (JP)

(72) Inventor: Masaaki Oosake, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 385 days.

(21) Appl. No.: 16/586,489

(22) Filed: Sep. 27, 2019

(65) Prior Publication Data

US 2020/0022560 A1 Jan. 23, 2020

Related U.S. Application Data

(63) Continuation of application No. PCT/JP2018/010568, filed on Mar. 16, 2018.

(30) Foreign Application Priority Data

Mar. 30, 2017 (JP) .............................. JP2017-066671

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00045* (2013.01); *A61B 1/041* (2013.01);
(Continued)

(58) Field of Classification Search
CPC . A61B 1/00009; A61B 1/00045; A61B 1/041; A61B 1/05; A61B 1/0684;
(Continued)

(56) References Cited

U.S. PATENT DOCUMENTS

2004/0003001 A1* 1/2004 Shimura ................. G16H 30/20
2007/0195165 A1* 8/2007 Hirakawa .......... A61B 1/00045
348/75

(Continued)

FOREIGN PATENT DOCUMENTS

CN 101373479 A 2/2009
CN 102695446 A 9/2012
(Continued)

OTHER PUBLICATIONS

Chinese Office Action for corresponding Chinese Application No. 201880022503.5, dated Jul. 27, 2021, with English translation.
(Continued)

*Primary Examiner* — Timothy J Neal
*Assistant Examiner* — Sung Ham
(74) *Attorney, Agent, or Firm* — Birch, Stewart, Kolasch & Birch, LLP

(57) ABSTRACT

Provided are a medical image processing device, an endoscope system, and a method of operating a medical image processing device that can enhance the reliability for recognition results obtained by recognition processing in a case where a lesioned part or the like is diagnosed by recognition processing of artificial intelligence (AI). Comparison between a first medical image and a second medical image to be a comparison target with respect to the first medical image is performed. A specific medical image selected in accordance with a result of the comparison from among the second medical images is acquired. A monitor displays a plurality of recognition results that are obtained from recognition processing that is performed with respect to the specific medical image and performed for recognizing the observation target.

16 Claims, 14 Drawing Sheets

(51) Int. Cl.
  *A61B 1/05* (2006.01)
  *A61B 1/06* (2006.01)
  *A61B 5/103* (2006.01)
  *G06T 7/00* (2017.01)
(52) U.S. Cl.
  CPC .............. *A61B 1/05* (2013.01); *A61B 1/0684* (2013.01); *A61B 5/1032* (2013.01); *G06T 7/0012* (2013.01); *G06T 2207/10024* (2013.01); *G06T 2207/10068* (2013.01); *G06T 2207/30096* (2013.01)
(58) Field of Classification Search
  CPC ..... A61B 5/1032; A61B 1/0005; A61B 1/045; A61B 1/0638; A61B 1/00; A61B 1/00096; A61B 1/00188; A61B 1/0669; A61B 1/043; A61B 1/0646; A61B 1/0653; G06T 7/0012; G06T 2207/10024; G06T 2207/10068; G06T 2207/30096; G06T 2207/30028; G06T 2207/30168; G06T 2207/10152; G06T 2207/30101
  USPC ................................................. 382/128–134
  See application file for complete search history.

(56) References Cited

U.S. PATENT DOCUMENTS

| | | | | |
|---|---|---|---|---|
| 2008/0243395 | A1* | 10/2008 | Oosawa | G16H 70/60 702/19 |
| 2009/0312607 | A1* | 12/2009 | Sunagawa | A61B 5/0071 600/160 |
| 2010/0232661 | A1* | 9/2010 | Hisanaga | G06K 9/00 382/128 |
| 2011/0245642 | A1* | 10/2011 | Minetoma | A61B 5/0084 600/324 |
| 2011/0317043 | A1* | 12/2011 | On | H04N 5/2256 348/241 |
| 2012/0327205 | A1 | 12/2012 | Takahashi | |
| 2013/0114867 | A1* | 5/2013 | Kondo | G16H 30/40 382/128 |
| 2014/0376792 | A1* | 12/2014 | Matsuzaki | A61B 1/00009 382/128 |
| 2015/0208958 | A1* | 7/2015 | Kaku | A61B 1/043 600/339 |
| 2015/0272429 | A1* | 10/2015 | Shigeta | A61B 1/0655 348/65 |
| 2015/0356245 | A1* | 12/2015 | Kozu | G16H 50/70 705/2 |
| 2015/0356271 | A1* | 12/2015 | Kozu | G16H 30/40 705/2 |
| 2015/0374218 | A1 | 12/2015 | Nishio et al. | |
| 2016/0055394 | A1* | 2/2016 | Kanada | G06F 16/532 382/128 |
| 2016/0174886 | A1* | 6/2016 | Shiraishi | A61B 1/000094 600/339 |
| 2017/0039450 | A1 | 2/2017 | Zhou et al. | |
| 2017/0112356 | A1* | 4/2017 | Mitsui | A61B 1/00186 |
| 2018/0008134 | A1 | 1/2018 | Morita et al. | |
| 2018/0137634 | A1* | 5/2018 | Fujiwara | G06T 7/00 |

FOREIGN PATENT DOCUMENTS

| | | |
|---|---|---|
| CN | 103561632 A | 2/2014 |
| CN | 103745217 A | 4/2014 |
| CN | 104203065 A | 12/2014 |
| CN | 104462481 A | 3/2015 |
| CN | 104899891 A | 9/2015 |
| CN | 105023027 A | 11/2015 |
| CN | 105025774 A | 11/2015 |
| CN | 105045818 A | 11/2015 |
| CN | 105320705 A | 2/2016 |
| CN | 105488478 A | 4/2016 |
| CN | 105930515 A | 9/2016 |
| CN | 106021542 A | 10/2016 |
| CN | 106255966 A | 12/2016 |
| CN | 106295687 A | 1/2017 |
| EP | 2823749 A1 | 1/2015 |
| EP | 3028624 A1 | 6/2016 |
| JP | 2001-325294 A | 11/2001 |
| JP | 2004-5364 A | 1/2004 |
| JP | 2007-275216 A | 10/2007 |
| JP | 2007-280229 A | 10/2007 |
| JP | 2008-197917 A | 8/2008 |
| JP | 2011-217798 A | 11/2011 |
| WO | WO 2014/120727 A2 | 8/2014 |
| WO | WO 2015/045576 A1 | 4/2015 |

OTHER PUBLICATIONS

Extended European Search Report, dated Mar. 9, 2020, for corresponding European Application No. 18777155.5.
Chinese Office Action and Search Report for corresponding Chinese Application No. 201880022503.5, dated Apr. 6, 2021, with English translation of the Office Action.
International Preliminary Report on Patentability (Form PCT/IPEA/409) for International Application No. PCT/JP2018/010568, dated Mar. 28, 2019, with English translation.
International Search Report and Written Opinion of the International Searching Authority (Forms PCT/ISA/210 and PCT/ISA/237) for International Application No. PCT/JP2018/010568, dated May 15, 2018, with an English translation of the International Search Report.
Japanese Office Action, dated Feb. 18, 2020, for corresponding Japanese Application No. 2019-509303, with an English translation.
Chinese Office Action for correspondinq Chinese Application No. 201880022503.5. dated Oct. 29, 2021, with English translation.

* cited by examiner

MEDICAL IMAGE PROCESSOR, ENDOSCOPE SYSTEM, AND METHOD OF OPERATING MEDICAL IMAGE PROCESSOR

CROSS-REFERENCE TO RELATED APPLICATIONS

This application is a Continuation of PCT International Application No. PCT/JP2018/010568 filed on 16 Mar. 2018, which claims priority under 35 U.S.C § 119(a) to Japanese Patent Application No. 2017-066671 filed on 30 Mar. 2017. The above application is hereby expressly incorporated by reference, in its entirety, into the present application.

BACKGROUND OF THE INVENTION

1. Field of the Invention

The present invention relates to a medical image processing device, an endoscope system, and a method of operating a medical image processing device for supporting discrimination of an observation target, such as discrimination of the progression degree of a lesioned part.

2. Description of the Related Art

In the medical field, diagnosis of a patient's medical condition and image diagnosis, such as follow-up observation, are performed using an endoscope image, an X-ray image, a computed tomography (CT) image, and a magnetic resonance (MR) image. Doctors or the like perform a decision of treatment policy on the basis of such image diagnosis. However, in a case where a person who performs image diagnosis, such as a doctor, is inexperienced, or even if the person is experienced, in a case where an image to be a diagnosis target is a rare case and is out of his/her specialized field, there is a case where it is difficult for the doctor to reliably perform the image diagnosis.

In such a situation, using images of past cases in conformity with an image acquired during diagnosis is performed in order to compensate for inexperience of the doctor or the like. For example, in JP2001-325294A and JP2004-005364A (corresponding to U.S. Pat. No. 7,374,077B2), past case images of which the similarities of image feature amounts are high are retrieved from the past case images stored in a database, and the retrieved past case images are displayed on a display device.

SUMMARY OF THE INVENTION

In recent years, automatically diagnosing an observation target is being performed by recognition processing for mechanically recognizing the observation target, such as artificial intelligence (AI). By using such recognition processing, the doctor's inexperience can be compensated for, and an objective diagnostic result can be obtained excluding subjective determination. However, in a case where the recognition processing used for diagnosis is not general on the medical spot and has not gained sufficient reliability, it is considered that a recognition result obtained by the recognition processing is not regarded as important. Hence, in a case where a lesioned part or the like is diagnosed by the recognition processing, it has been required to enhance the reliability of the recognition processing.

In addition, JP2001-325294A and JP2004-005364A describe that the diagnostic result is presented together with the past case images. However, it is considered that the diagnostic result is a result obtained on the basis of the doctor's subjective determination and has variations depending on doctors. Even in order to eliminate such variations in diagnostic result by the doctors, performing more objective diagnosis is required using the recognition result obtained by the recognition processing.

An object of the invention is to provide a medical image processing device, an endoscope system, and a method of operating a medical image processing device that can enhance the reliability for recognition results obtained by recognition processing in a case where a lesioned part or the like is diagnosed by recognition processing of artificial intelligence (AI).

A medical image processing device of the invention comprises a medical image acquisition unit, a medical image selection unit, and a display control unit. The medical image acquisition unit acquires a first medical image that is obtained by imaging an observation target by an imaging unit. The medical image selection unit performs comparison between the first medical image and a second medical image to be a comparison target with respect to the first medical image, and acquires a specific medical image selected in accordance with a result of the comparison from among the second medical images. The display control unit displays a plurality of recognition results, which are obtained from recognition processing that is performed with respect to the specific medical image and performed for recognizing the observation target, on a display unit.

It is preferable that the medical image selection unit compares a feature amount of the first medical image with a feature amount of the second medical image, and selects the specific medical image in accordance with a similarity between the feature amounts. It is preferable that the feature amount is at least any one of a blood vessel density, a blood vessel shape, a blood vessel branch number, a blood vessel thickness, a blood vessel length a blood vessel meandering degree, a blood vessel invasion degree, a gland duct shape, a gland duct opening shape, a gland duct length, a gland duct meandering degree, or color information, or a value obtained by combining two or more thereof.

It is preferable that a plurality of kinds of the recognition results are present, and the display control unit displays a ratio of the recognition results for each kind on the display unit. It is preferable that a plurality of kinds of the recognition results are present, and the display control unit displays the number of the recognition results on the display unit for each kind. It is preferable that the display control unit also displays a user recognition result, which is recorded in association with the second medical image and is obtained by determining the observation target by a user, on the display unit. It is preferable that the recognition results include a recognition result, which is recorded in association with the second medical image and is obtained by performing recognition processing in another medical image processing device. It is preferable that the recognition results include at least the observation target being a lesioned part and the observation target being a normal part. It is preferable that the recognition results of the recognition processing are multiple kinds.

It is preferable that the second medical image is registered in advance in a medical image storage unit. It is preferable that the second medical image is obtained by imaging with the imaging unit at a timing before the first medical image. It is preferable that the second medical image is obtained by imaging with the imaging unit at a timing after the first medical image.

It is preferable that the second medical image is obtained by imaging the observation target illuminated with special light. It is preferable that the special light has a wavelength range of 450 nm or less. It is preferable that the second medical image includes a plurality of images having different magnification factors for the same observation target.

An endoscope system of the invention comprises a light source device, an endoscope, a medical image acquisition unit, a medical image selection unit, and a display unit. The light source device generates illumination light for illuminating an observation target. The endoscope has an imaging unit that images the observation target illuminated with the illumination light. The medical image acquisition unit acquires a first medical image that is obtained by imaging an observation target by an imaging unit. The medical image selection unit performs comparison between the first medical image and a second medical image to be a comparison target with respect to the first medical image, and acquires a specific medical image selected in accordance with a result of the comparison from among the second medical images. The display control unit displays a plurality of recognition results, which are obtained from recognition processing that is performed with respect to the specific medical image and performed for recognizing the observation target, on a display unit.

A method of operating a medical image processor of the invention has a medical image acquisition step, a medical image selection step, and a display step. In the medical image acquisition step, the medical image acquisition unit acquires a first medical image by imaging an observation target by an imaging unit. In the medical image selection step, the medical image selection unit performs comparison between the first medical image and a second medical image to be a comparison target with respect to the first medical image, and acquires a specific medical image selected in accordance with a result of the comparison from among the second medical images. In the display control step, the display control unit displays a plurality of recognition results, which are obtained from recognition processing that is performed with respect to the specific medical image and performed for recognizing the observation target, on a display unit.

According to the invention, the reliability for recognition results obtained by recognition processing can be enhanced in a case where a lesioned part or the like is diagnosed by recognition processing of artificial intelligence (AI).

DESCRIPTION OF THE PREFERRED EMBODIMENTS

First Embodiment

Figure 1:
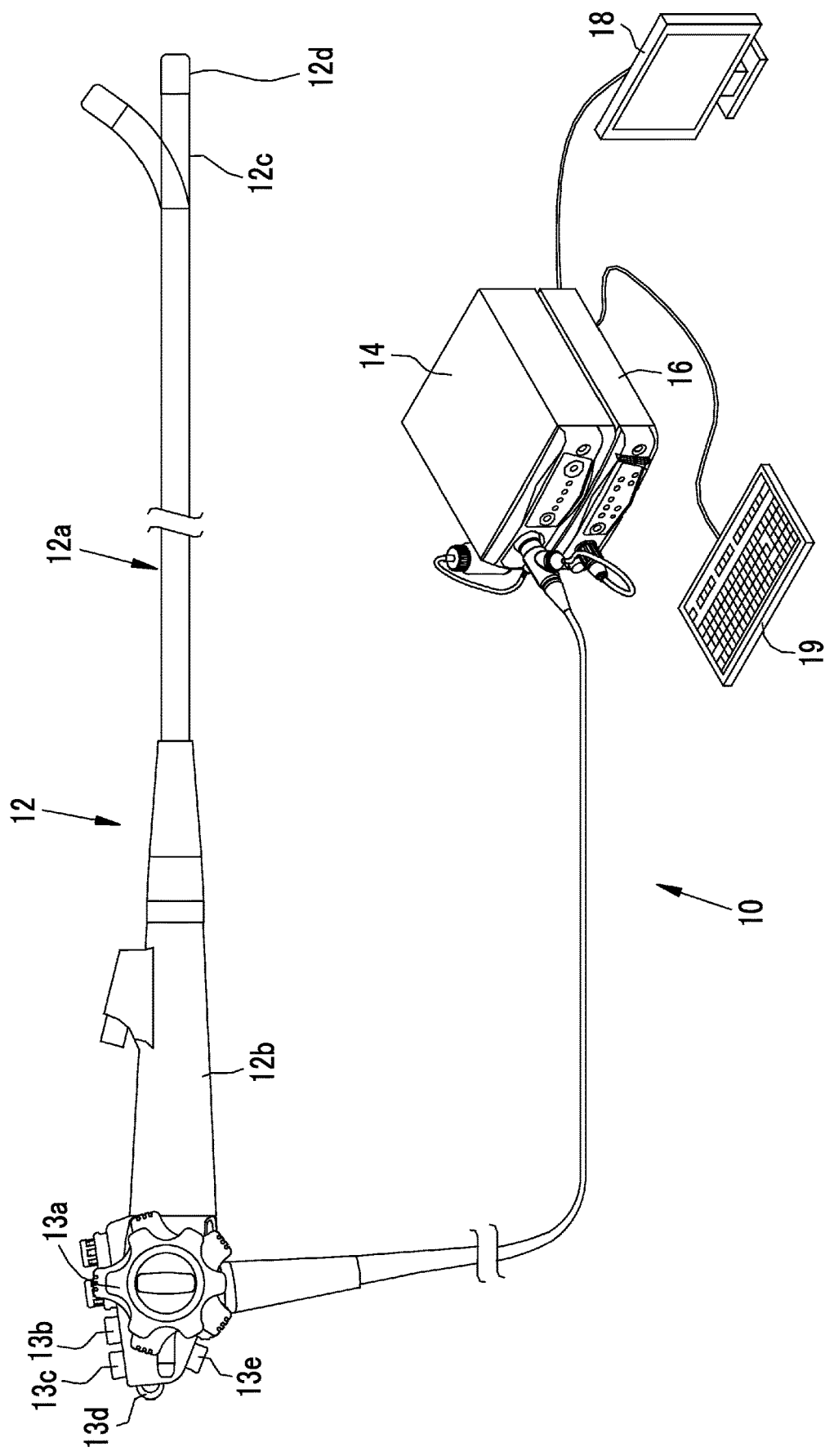
FIG. 1 is an external view of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14, and is electrically connected to the processor device 16. The endoscope 12 has an insertion part 12a to be inserted into a subject, an operating part 12b provided at a proximal end portion of the insertion part 12a, and a bending part 12c and a distal end part 12d provided on a distal end side of the insertion part 12a. By operating an angle knob 13a of the operating part 12b, the bending part 12c makes a bending motion. The distal end part 12d is directed in a desired direction by this bending motion.

Additionally, the operating part 12b is provided with a still image acquisition unit 13b used for operating the acquisition of still images, a mode switching unit 13c used for operating the switching of observation modes, and a zooming operating unit 13d used for operating the change of a zoom magnification factor, in addition to the angle knob 13a. In the still image acquisition unit 13b, a freeze operation of displaying a still image of an observation target on the monitor 18, and a release operation of saving the still image in a storage are possible.

The endoscope system 10 has a normal mode, a special mode, and a discrimination mode as the observation modes. In a case where an observation mode is the normal mode, normal light obtained by combining a plurality of colors of light components together in a quantity-of-light ratio Lc for normal mode is emitted, and a normal image is displayed on a monitor 18 on the basis of image signals obtained by imaging the observation target under illumination with this normal light. Additionally, in a case where an observation mode is the special mode, special light obtained by combining a plurality of colors of light components together in a quantity-of-light ratio Ls for special mode is emitted, and a special image is displayed on the monitor 18 on the basis of image signals obtained by imaging the observation target under illumination with this special light.

Additionally, in a case where an observation mode is the discrimination support mode, discrimination support mode illumination light is emitted. In the present embodiment, the normal light is emitted as the discrimination support mode illumination light. However, the special light may be emitted. From an image obtained by imaging the observation target under illumination with this discrimination support mode illumination light, a discrimination support image for supporting the discrimination of the observation target is generated, and is displayed on the monitor 18.

The processor device 16 is electrically connected to the monitor 18 and the console 19. The monitor 18 outputs and displays an image of the observation target, information accompanying the image, and the like. The console 19 functions as a user interface that receives input operations, such as designation or the like of a region of interest (ROI) and function setting.

Figure 2:
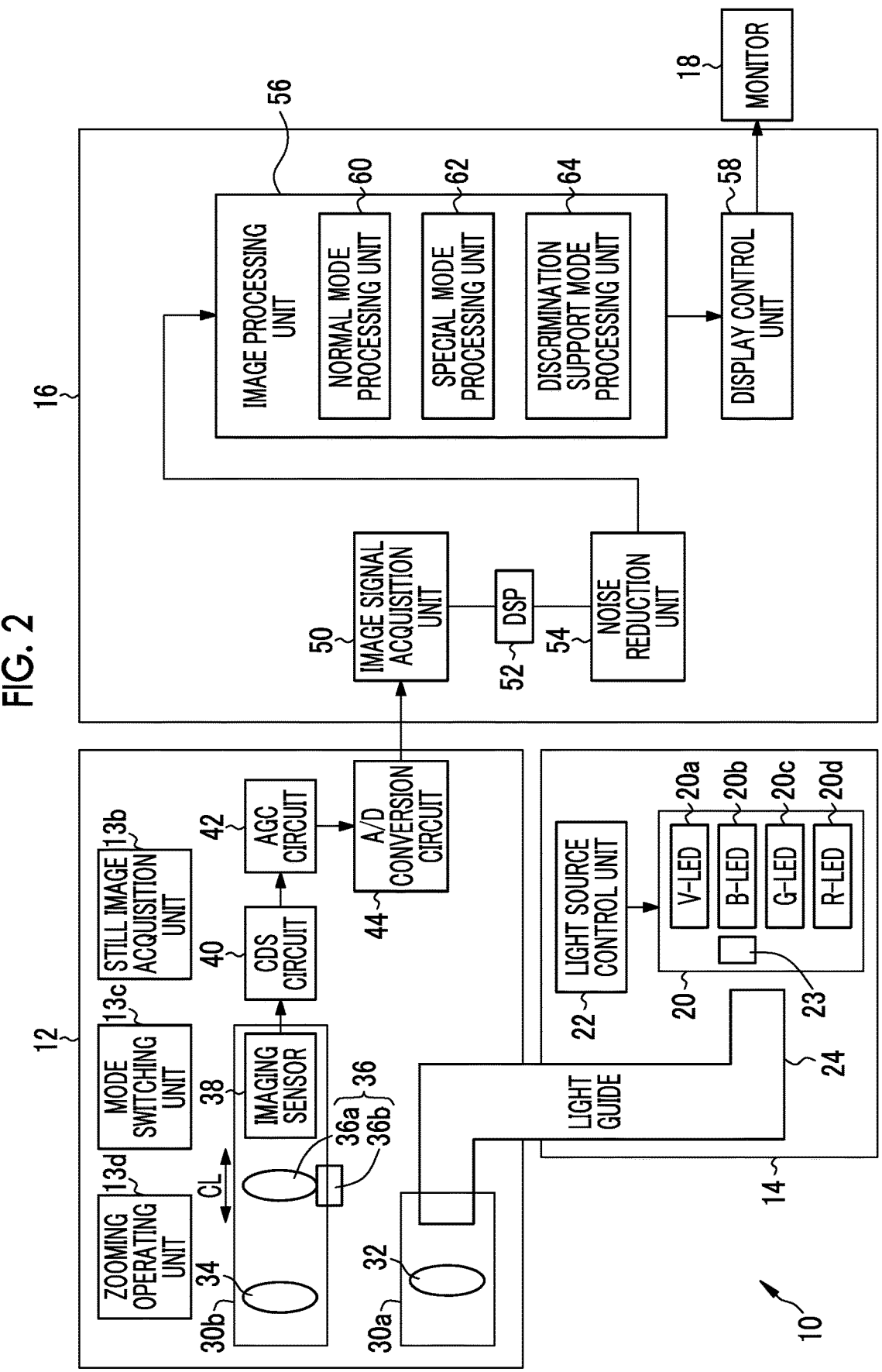
FIG. 2 is a block diagram illustrating the functions of an endoscope system of a third embodiment comprising a plurality of LED light sources.

As illustrated in FIG. 2, the light source device 14 comprises a light source unit 20 that emits the illumination light to be used for illumination of the observation target, and a light source control unit 22 that controls the light source unit 20. The light source unit 20 is semiconductor light sources, such as a plurality of colors of light emitting diodes (LEDs). The light source control unit 22 controls the quantity of light emission of the illumination light by ON/OFF of the LEDs and the adjustment of the driving currents or driving voltages of the LEDs. Additionally, the light source control unit 22 controls the wavelength range of the illumination light, for example, by changing the optical filters.

Figure 3:
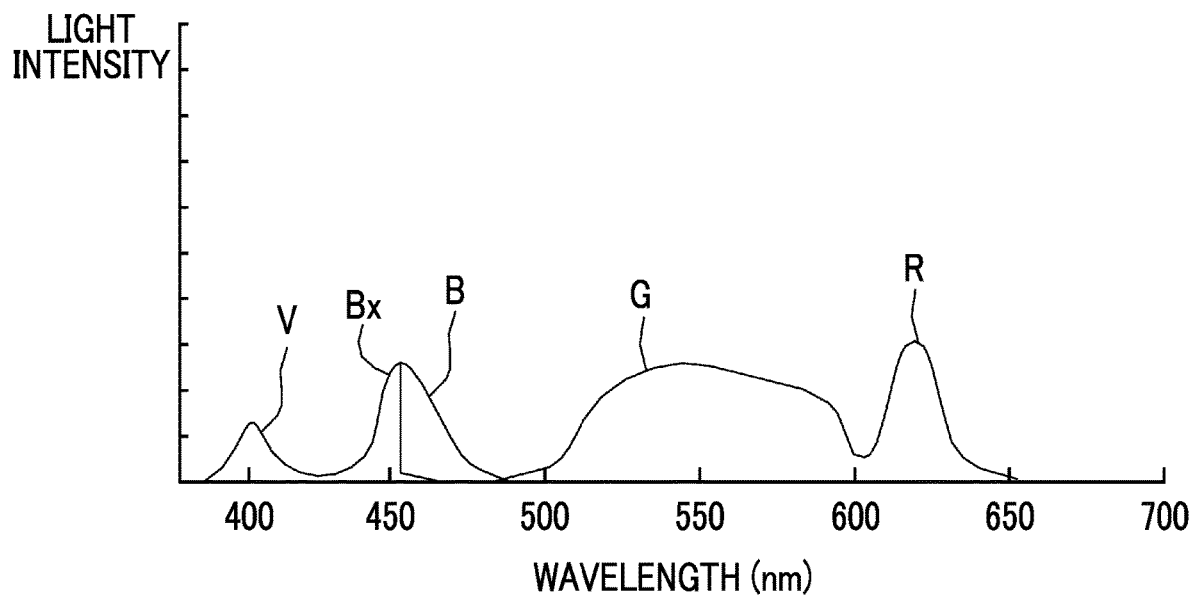
FIG. 3 is a graph illustrating the spectroscopic spectrum of violet light V, blue light B, blue light Bx, green light G, and red light R.

In the first embodiment, the light source unit 20 has four color LEDs of a violet light emitting diode (V-LED) 20a, a blue light emitting diode (B-LED) 20b, a green light emitting diode (G-LED) 20c, a red light emitting diode (R-LED) 20d, and a wavelength cutoff filter 23. As illustrated in FIG. 3, the V-LED 20a emits violet light V having a wavelength range of 380 nm to 420 nm.

The B-LED 20b emits blue light B having a wavelength range of 420 nm to 500 nm. The blue light B emitted from the B-LED 23b is cut by the wavelength cutoff filter 23 on at least a longer wavelength side than the peak wavelength of 450 nm. Accordingly, the blue light Bx after being transmitted through the wavelength cutoff filter 23 has a wavelength range of 420 to 460 nm. In this way, the reason why light in a wavelength range on the longer wavelength side than 460 nm is cut is that the light in the wavelength range on the longer wavelength side than 460 nm is a factor in which the blood vessel contrast of blood vessels that is the observation target is lowered. In addition, the wavelength cutoff filter 23 may reduce the light in the wavelength range on the longer wavelength side than 460 nm instead of cutting the light in the wavelength range on the longer wavelength side than 460 nm.

The G-LED 20c emits green light G having a wavelength range of 480 nm to 600 nm. The R-LED 20d emits red light R having a wavelength range of 600 nm to 650 nm. In addition, center wavelengths and peak wavelengths of the respective color lights emitted from the LEDs 20a to 20d may be the same as each other or may be different from each other.

The light source control unit 22 independently controls ON/OFF of the respective LEDs 20a to 20d, the quantity of light emission at the time of ON, and the like, thereby adjusting the light emission timing of illumination light, a light emission period, the quantity of light, and a spectroscopic spectrum. The control of ON and OFF in the light source control unit 22 varies in the respective observation modes. In addition, the reference brightness is capable of being set by a brightness setting unit of the light source device 14, the console 19, or the like.

Figure 4:
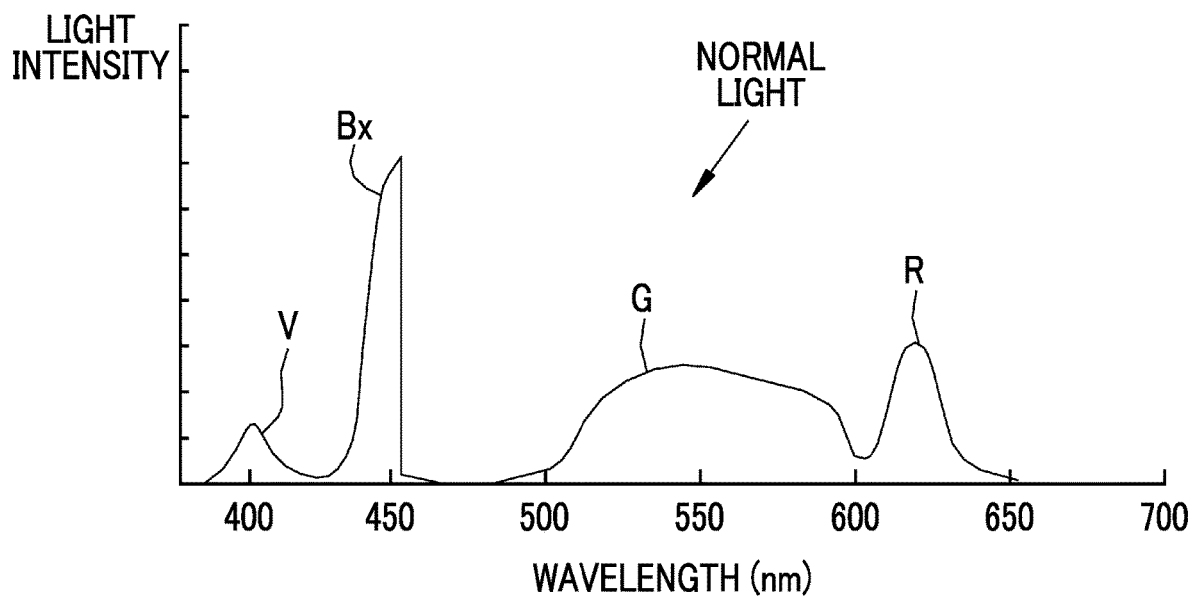
FIG. 4 is a graph illustrating the spectroscopic spectrum of normal light of the first embodiment.

In the case of the normal mode or the discrimination support mode, the light source control unit 22 turns on the V-LED 20a, the B-LED 20b, the G-LED 20c, and the R-LED 20d altogether. In that case, as illustrated in FIG. 4, the quantity-of-light ratio Lc between the violet light V, the blue light B, the green light G, and the red light R is set such that the peak of the light intensity of the blue light Bx becomes larger than the light intensity of any of the violet light V, the green light G, and the red light R. Accordingly, in the normal mode or the discrimination support mode, multicolor light for normal mode or discrimination support mode including the violet light V, the blue light Bx, the green light G, and the red light R is emitted as the normal light from the light source device 14. Since the normal light has an intensity equal to or more than a given level from a blue range to a red range, the normal light is substantially white.

Figure 5:
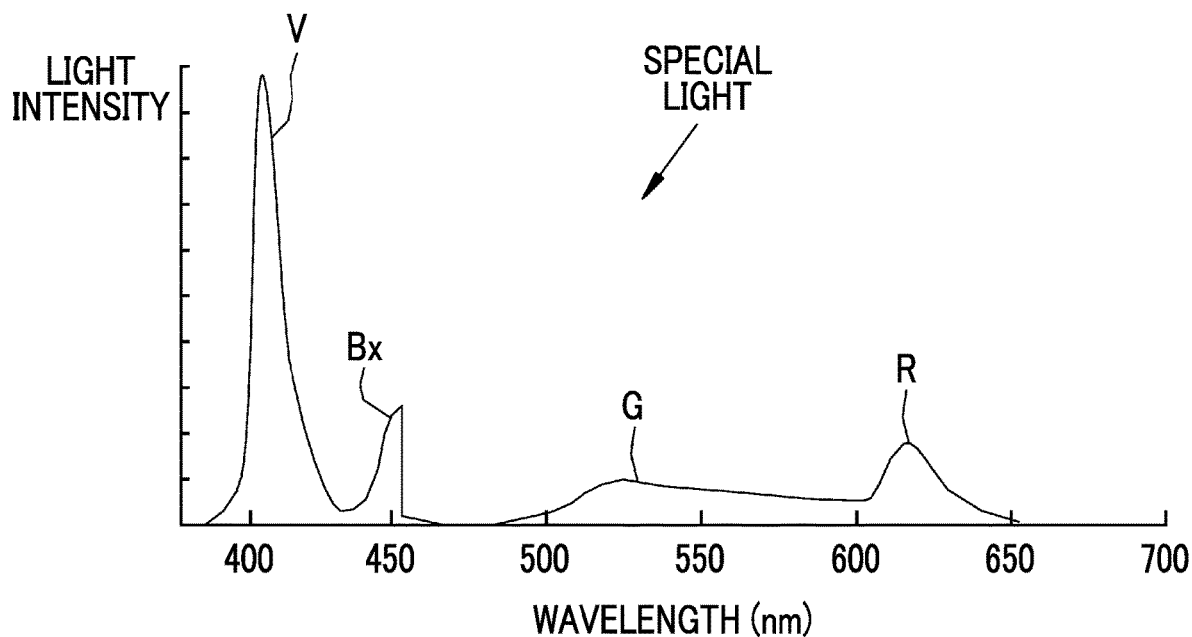
FIG. 5 is a graph illustrating the spectroscopic spectrum of special light of the first embodiment.

In the case of the special mode, the light source control unit 22 turns on the V-LED 20a, the B-LED 20b, the G-LED 20c, and the R-LED 20d altogether. In that case, as illustrated in FIG. 5, the quantity-of-light ratio Ls between the violet light V, the blue light B, the green light G, and the red light R is set such that the peak of the light intensity of the purple light V becomes larger than the light intensity of any of the blue light Bx, the green light G, and the red light R. Additionally, the peak of the light intensity of the green light G and the red light R is set to be smaller than the peak of the light intensity of the purple light V and the blue light Bx. Accordingly, in the special mode, multicolor light for special mode including the violet light V, the blue light Bx, the green light G, and the red light R is emitted as the special light from the light source device 14. Since the proportion of the purple light V is large, the special light is bluish light. In addition, the special light may not include light of all four colors, and may include light from at least one color LED of the four color LEDs 20a to 20d. Additionally, it is preferable that the special light has a main wavelength range, for example, a peak wavelength or a center wavelength of 450 nm or less.

As illustrated in FIG. 2, the illumination light emitted from the light source unit 20 enters a light guide 24 inserted into the insertion part 12a via a light path coupling part (not illustrated) formed with a mirror, a lens, or the like. The light guide 24 is built in the endoscope 12 and a universal cord, and propagates the illumination light up to the distal end part 12d of the endoscope 12. The universal cord is a cord that connects the endoscope 12, and the light source device 14 and the processor device 16 together. In addition, multimode fiber can be used as the light guide 24. As an example, a fine-diameter fiber cable of which the core diameter is 105 μm, the clad diameter is 125 μm, and a diameter including a protective layer used as an outer cover is ϕ0.3 mm to ϕ0.5 mm can be used for the light guide 24.

The distal end part 12d of the endoscope 12 is provided with an illumination optical system 30a and an imaging optical system 30b. The illumination optical system 30a has an illumination lens 32. The observation target is illuminated with the illumination light propagated through the light guide 24 via the illumination lens 32. The imaging optical system 30b has an objective lens 34, a magnifying optical system 36, and an imaging sensor 38 (corresponding to "an imaging unit" of the invention). Various kinds of light, such as reflected light, scattered light, and fluorescent light from the observation target, enter the imaging sensor 38 via the objective lens 34 and the magnifying optical system 36. Accordingly, the image of the observation target is formed on the imaging sensor 38.

The magnifying optical system 36 comprises a zoom lens 36a that magnifies the observation target, and a lens drive unit 36b that moves the zoom lens 36a in an optical axis direction CL. The zoom lens 36a magnifies or reduces the observation target of which the image is formed on the imaging sensor 38 by freely moving between a telephoto end and a wide end in accordance with a zoom control performed by the lens drive unit 36b.

The imaging sensor 38 is a color imaging sensor that images the observation target irradiated with the illumination light. Each pixel of the imaging sensor 38 is provided with any one of a red (R) color filter, a green (G) color filter, and a blue (B) color filter. The imaging sensor 38 receives blue light with the B pixel provided with the B color filter from violet, receives green light with a G pixel provided with the G color filter, and receives red light with an R pixel provided with the R color filter. Image signals of respective RGB colors are output from the respective color pixels. The imaging sensor 38 transmits the output image signals to a CDS circuit 40.

In the normal mode or the discrimination support mode, the imaging sensor 38 images the observation target illuminated with the normal light, thereby outputting a Bc image signal from the B pixel, outputting a Gc image signal from the G pixel, and outputting an Rc image signal from the R pixel. Additionally, in the special mode, the imaging sensor 38 images the observation target illuminated with the special light, thereby outputting a Bs image signal from the B pixel, outputting a Gs image signal from the G pixel, and outputting an Rs image signal from the R pixel.

As the imaging sensor 38, a charge coupled device (CCD) imaging sensor, a complementary metal-oxide semiconductor (CMOS) imaging sensor, or the like is available. Additionally, instead of the imaging sensor 38 provided with the color filters in the primary colors of RGB, a complementary color imaging sensor including complementary color filters in C (cyan), M (magenta), Y (yellow), and G (green) may be used. In a case where the complementary color imaging sensor is used, image signals of four colors of CMYG are output. For this reason, the same respective RGB image signals as those in the imaging sensor 38 can be obtained by converting the image signals of four colors of CMYG into image signals of three colors of RGB through color conversion between complementary colors and the primary colors. Additionally, instead of the imaging sensor 38, a monochrome sensor that is not provided with the color filters may be used.

The CDS circuit 40 performs correlated double sampling (CDS) on analog image signals received from the imaging sensor 38. The image signals that have passed through the CDS circuit 40 are input to the AGC circuit 42. The AGC circuit 42 performs an automatic gain control (AGC) on the input image signals. An analog-to-digital (A/D) conversion circuit 44 converts the analog image signals, which have passed through the AGC circuit 42, into digital image signals. The A/D conversion circuit 44 inputs the digital image signals after the A/D conversion to the processor device 16.

As illustrated in FIG. 2, the processor device 16 comprises an image signal acquisition unit 50 (corresponding to "a medical image acquisition unit of the invention), a digital signal processor (DSP) 52, a noise reduction unit 54, an image processing unit 56, and a display control unit 58.

The image signal acquisition unit 50 acquires the digital image signals corresponding to an observation mode from the endoscope 12. In the case of the normal mode or the discrimination support mode, the Bc image signal, the Gc image signal, and the Rc image signal are acquired. In the case of the special mode, the Bs image signal, the Gs image signal, and the Rs image signal are acquired. In the case of the discrimination support mode, the Bc image signal, the Gc image signal, and the Rc image signal for one frame are acquired during the illumination of the normal light, and the Bs image signal, the Gs image signal, and the Rs image signals for one frame are acquired during the illumination of the special light.

The DSP 52 performs various kinds of signal processing, such as defect correction processing, offset processing, DSP gain correction processing, linear matrix processing, gamma conversion processing, demosaicing processing, and the like, on the image signals acquired by the image signal acquisition unit 50. In the defect correction processing, a signal of a defective pixel of the imaging sensor 38 is corrected. In the offset processing, a dark current component is removed from the image signals subjected to the defect correction processing, and an accurate zero level is set. In the DSP gain correction processing, a signal level is adjusted by multiplying the image signals subjected to the offset processing by a specific DSP gain.

The linear matrix processing enhances color reproducibility on the image signals subjected to the DSP gain correction processing. In the gamma conversion processing, brightness and saturation of the image signals subjected to the linear matrix processing are adjusted. By performing the demosaicing processing (also referred to as equalization processing or synchronization processing) on the image signals subjected to the gamma conversion processing, a signal of a color that runs short in each pixel is generated by interpolation. By means of this demosaicing processing, all pixels have signals of respective RGB colors. The noise reduction unit 54 performs noise reducing processing using, for example, a moving average method, a median filter method, or the like on the image signals subjected to the demosaicing processing or the like by the DSP 52, and reduces noise. The image signals after the noise reduction are input to the image processing unit 56.

The image processing unit 56 includes a normal mode processing unit 60, a special mode processing unit 62, and a discrimination support mode processing unit 64. The normal mode processing unit 60 operates in a case where the normal mode is set, and performs color conversion processing, color enhancement processing, and structure enhancement processing on the received Bc image signal, Gc image signal, and Rc image signal. In the color conversion processing, color conversion processing is performed on the RGB image signals by 3×3 matrix processing, gradation transformation processing, three-dimensional look-up table (LUT) processing, and the like.

The color enhancement processing is performed on the RGB image signals subjected to the color conversion processing. The structure enhancement processing is the processing of enhancing the structure of the observation target, and is performed on the RGB image signals after the color enhancement processing. The normal image is obtained by performing the various kinds of image processing as described above. Since the normal image is an image obtained on the basis of the normal light in which the violet light V, the blue light Bx, the green light G, and the red light R are emitted in a well-balanced manner, the normal image is a natural-tone image. The normal image is input to the display control unit 58.

The special mode processing unit 62 operates in a case where the special mode is set. In the special mode processing unit 62, the color conversion processing, the color enhancement processing, and the structure enhancement processing is performed on the received Bs image signal, Gs image signal, and Rs image signal. The processing contents of the color conversion processing, the color enhancement processing, and the structure enhancement processing are the same as those of the normal mode processing unit 60. The special image is obtained by performing the various kinds of image processing as described above. Since the special image is an image obtained on the basis of the special light in which the violet light V with a high absorption coefficient of hemoglobin of blood vessels has a larger quantity of light emission than the blue light Bx, the green light G, and the red light R in the other colors, the resolution of a blood vessel structure or a glandular structure is higher than that of the other structures. The special image is input to the display control unit 58.

The discrimination support mode processing unit 64 operates in cases where the discrimination support mode is set. In the discrimination support mode processing unit 64, the same image processing as that of the normal mode processing unit 60, such as the color conversion processing, is performed on the received Bc image signal, Gc image signal, and Rc image signal. Then, a still image of the observation target obtained when the still image acquisition unit 13b is operated is acquired as the first medical image to be used for the discrimination of the observation target. This first medical image is compared with a second medical image to be a comparison target, and a discrimination support image for supporting the discrimination of the observation target is generated on the basis of the result of the comparison. In addition, the details of the discrimination support mode processing unit 64 will be described below.

The display control unit 58 performs a display control for displaying the image or data from the image processing unit 56 on the monitor 18. In a case where the normal mode, the display control unit 58 performs the control of displaying the normal image on the monitor 18. In a case where the special mode is set, the display control unit 58 performs the control of displaying the special image on the monitor 18. In a case where the discrimination support mode is set, the display control unit 58 performs the control of displaying the discrimination support image on the monitor 18.

Figure 6:
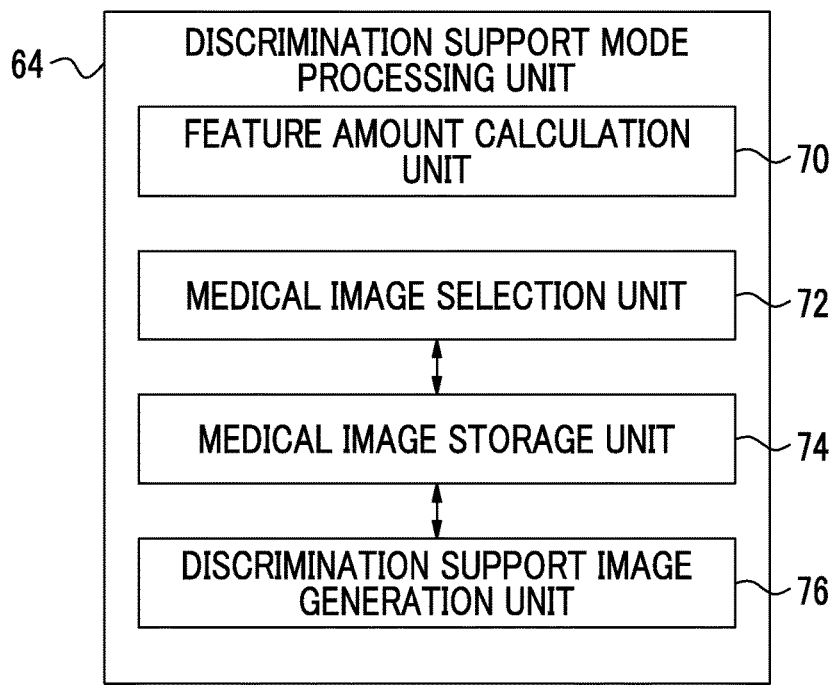
FIG. 6 is a block diagram illustrating the functions of a discrimination support mode processing unit comprising a medical image storage unit.

As illustrated in FIG. 6, the discrimination support mode processing unit 64 includes a feature amount calculation unit 70, a medical image selection unit 72, a medical image storage unit 74, and a discrimination support image generation unit 76. The feature amount calculation unit 70 calculates an image-like feature amount from the first medical image. As a method of calculating the feature amount, it is preferable to acquire the feature amount by Convolutional Neural Network or the like. Additionally, it is preferable that the feature amount is the shape or color of a predetermined spot in the observation target, an index value obtained from the shape or color, or the like. For example, it is preferable that the feature amount is at least any one of blood vessel density, blood vessel shape, the number of branches of the blood vessels, the thickness of the blood vessels, the degree of meandering of the blood vessels, the invasion depth of the blood vessels, gland duct shape, gland duct opening shape, the length of a gland duct, the degree of meandering of the gland duct, or color information, or a value obtained by combining two or more of them.

The medical image selection unit 72 performs the comparison processing of comparing the first medical image with second medical images stored in the medical image storage unit 74, and performs the image selection processing of selecting a specific medical image in accordance with a comparison result out of the second medical images. In addition, in the medical image storage unit 74, the second medical images and image-like feature amounts of the second medical images are stored in association with each other. However, a feature amount of a second medical image may be calculated whenever being compared with the first medical image instead of being stored in association with the second medical images in order to suppress the capacity in the medical image storage unit 74. Additionally, in the medical image storage unit 74, the second medical images are stored in association with recognition results that are obtained from the recognition processing that is performed on the second medical images and is performed for mechanically recognizing the observation target. The second medical images, and user recognition results obtained by a user subjectively having determined the observation target may also be stored in association in the medical image storage unit 74. However, similarly to the feature amounts, a recognition result may also be calculated whenever being compared with the first medical image instead of being stored in association with the second medical images. It is preferable that the recognition processing is machine learning processing of an artificial intelligence (AI) or the like.

In the medical image selection unit 72, in the comparison processing, a feature amount of the first medical image and the feature amounts of the second medical image are compared with each other, and the similarities between the first medical image and the second medical images are calculated. In the image selection processing, a second medical image in which the similarity of the feature amount satisfies a specific condition is selected as the specific medical image. Specifically, a second medical image in which the similarity of the feature amount with the first medical image is equal to or more than a given level from among the second medical images is selected as the specific medical image.

Figure 7:
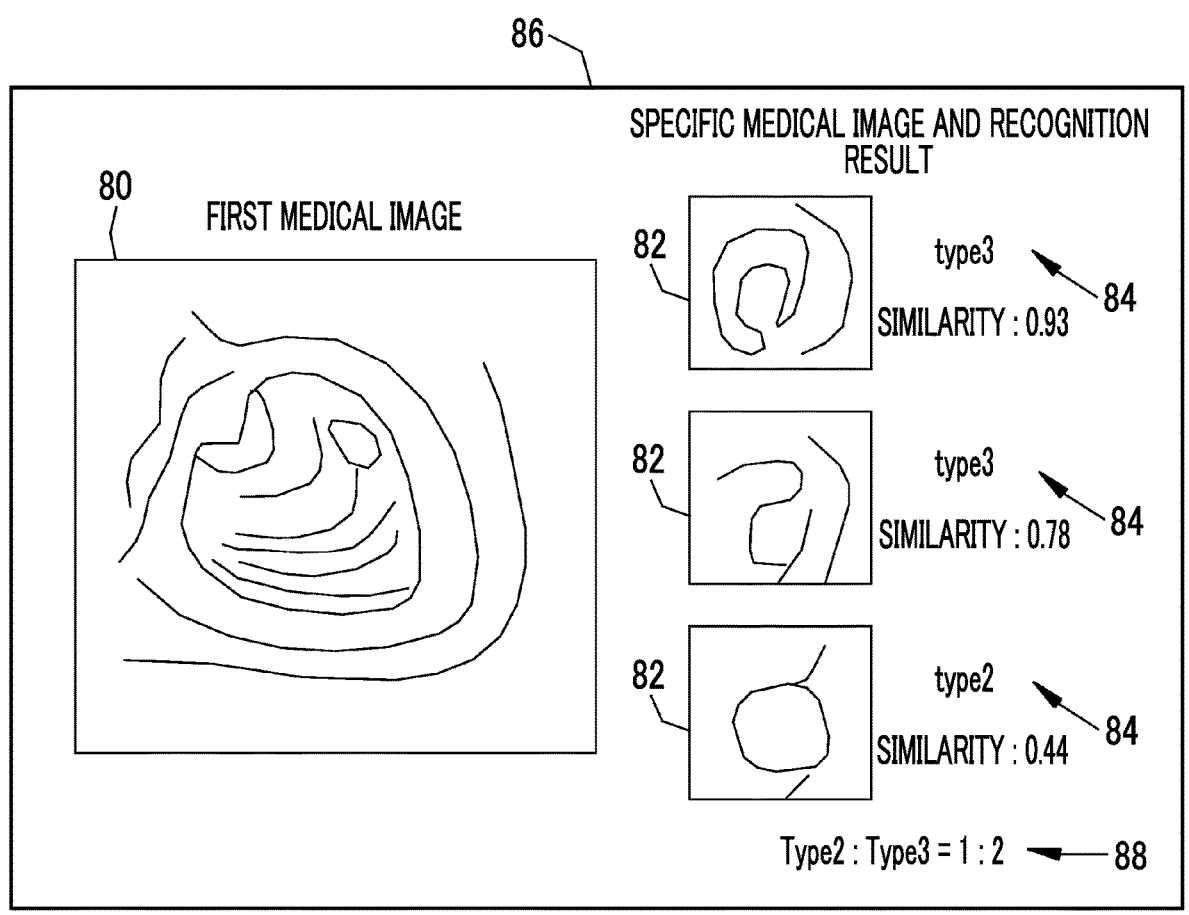
FIG. 7 is an image view illustrating a discrimination support image in a case where only normal light is used as discrimination support mode illumination light.

As illustrated in FIG. 7, the discrimination support image generation unit 76 generates a discrimination support image 86 in which a plurality of specific medical images 82 and a plurality of recognition results 84 of the recognition processing associated with the specific medical images 82 are displayed together with the first medical image 80. In the discrimination support image 86, the plurality of specific medical images 82 and the specific recognition results 84 thereof are displayed on the right of the first medical image. Additionally, similarities to the feature amount of the first medical image are also displayed together on the specific medical image 82, respectively, and specific medical images with high similarities are displayed on the upper side of the discrimination support image 86. In addition, the user recognition results other than the recognition results of the recognition processing may be displayed in the discrimination support image 86.

It is preferable that the recognition results of the recognition processing are multiple kinds. For example, it is preferable that the recognition results include the observation target being a lesioned part or a normal part, the kind, type, progression degree, and score of the lesioned part. In the discrimination support image 86 illustrated in FIG. 7, the kind of the lesioned part is the type of the lesioned part. Additionally, the recognition results may be recognition results obtained by performing the recognition processing that is the same as or different from the recognition processing in the endoscope system 10, in other medical image processors provided in other facilities different from the endoscope system 10.

By presenting a plurality of recognition results of the second medical images with high similarities to the first medical image, the discrimination of the observation target to be displayed in the first medical image can be performed. This is because a discrimination can be more reliably performed in a case where the plurality of recognition results of the second medical images obtained in the past similar cases are presented rather than independently presenting a recognition result obtained by performing the recognition processing on the first medical image.

Additionally, in the discrimination support image 86, a ratio 88 (Type 2:Type 3=1:2) of the types of lesioned parts is also displayed together as the ratio of the kinds of recognition results. By presenting the ratio of the kinds of recognition results with respect to the second medical images in this way, the discrimination of the observation target to be displayed on the first medical image is easily performed. In addition, in the discrimination support image 86, it is preferable to display the number of recognition results for each kind in addition to the ratio of the kinds of recognition results.

Figure 8:
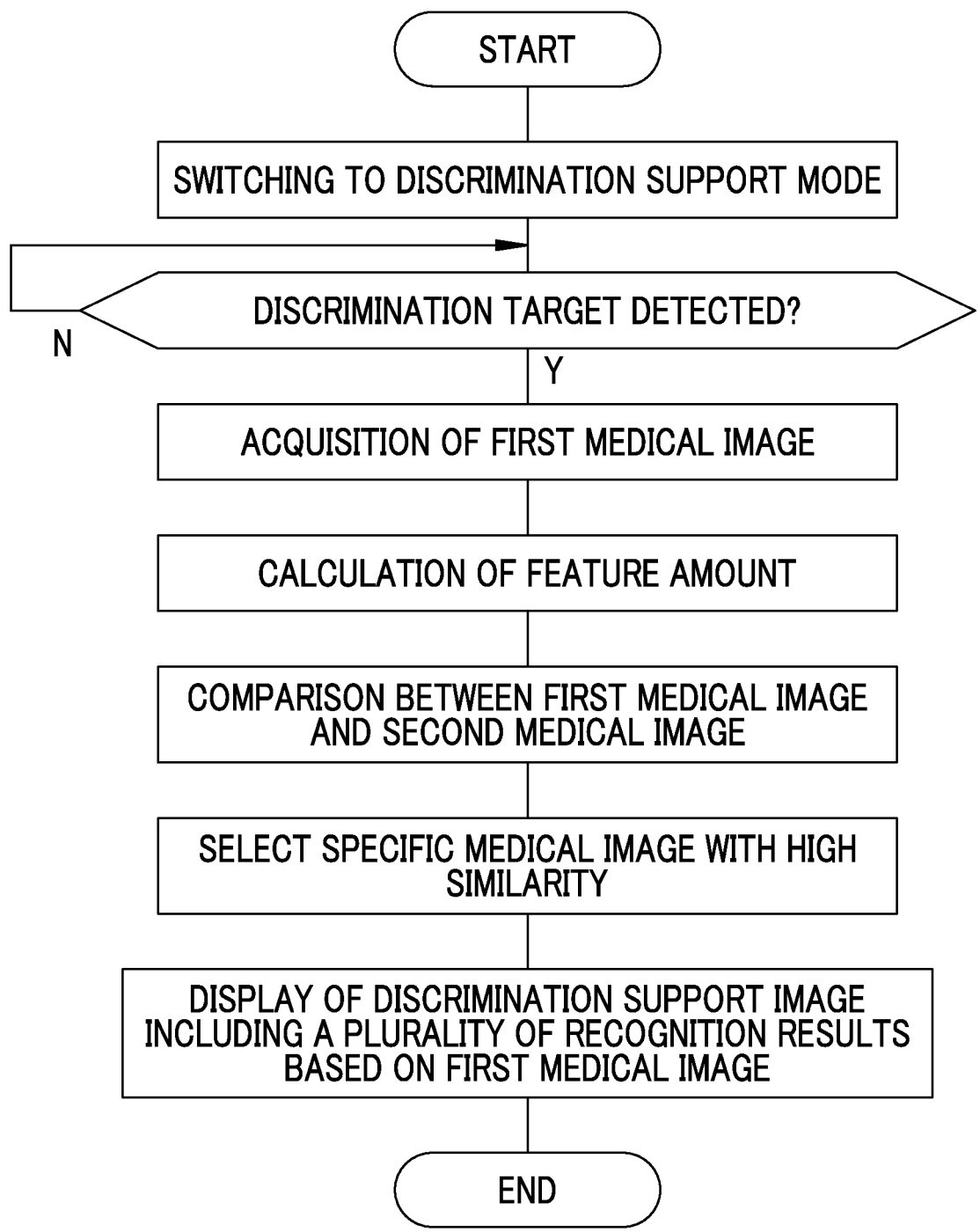
FIG. 8 is a flowchart illustrating a series of flow of the discrimination support mode in a case where the discrimination support mode illumination light is only the normal light.

Next, a series of flow of the discrimination support mode will be described along the flowchart illustrated in FIG. 8. The mode switching unit 13c is operated to perform switching to the discrimination support mode. Accordingly, the observation target is illuminated with the discrimination support mode illumination light. The observation target illuminated with the discrimination support mode illumination light is imaged by the imaging sensor 38, and a dynamic image of the observation target is displayed on the monitor 18. Then, in a case where the observation target to be a discrimination target is detected, the still image acquisition unit 13b is operated to acquire a still image of the observation target as the first medical image. Then, the image-like feature amount is calculated from the first medical image.

Next, the feature amounts of the second medical images stored in the medical image storage unit 74 are compared with the feature amount of the first medical image, and the similarities between the first medical image and the second medical images are calculated. A second medical image of which the similarity is equal to or higher than a given level is selected as the specific medical image. Then, the discrimination support image in which the plurality of specific medical images and the recognition results thereof are displayed together with the first medical image is generated. The generated discrimination support image is displayed on the monitor 18. In the discrimination support image, the recognition results are respectively displayed regarding the plurality of specific medical images, and the ratio and number of the kinds of recognition results are also displayed in combination. Therefore, the discrimination of the observation target can be reliably performed.

Second Embodiment

Figure 9:
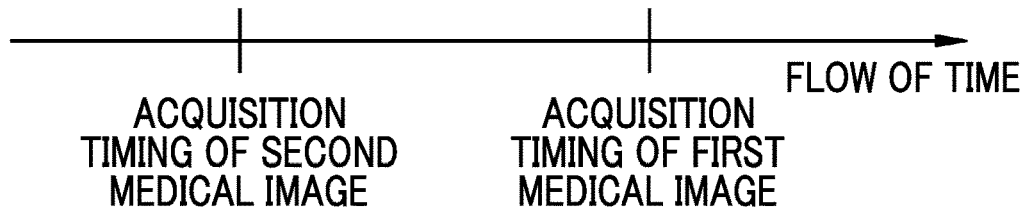
FIG. 9 is an explanatory view illustrating that the acquisition timing of a second medical image is before the acquisition timing of a first medical image.

In the first embodiment, the past second medical images stored in the medical image storage unit are used as the images to be compared with the first medical image. However, in the second embodiment, an image, which is acquired at a timing different from the first medical image through the same endoscope diagnosis as in the case where the first medical image is acquired, is used as a second medical image. Specifically, as illustrated in FIG. 9, an image acquired before a timing when the first medical image is acquired is used as a second medical image. It is preferable that, in modes other than the discrimination support mode, the second medical image is a still image of the observation target obtained by operating the still image acquisition unit 13b, or in the second medical images acquisition mode, the second medical image is a still image of the observation target obtained by operating the still image acquisition unit 13b. In addition, the second medical image acquisition mode is the same as that of the normal mode or the special mode except that a second medical image is acquired without performing the generation of the discrimination support image.

Figure 10:
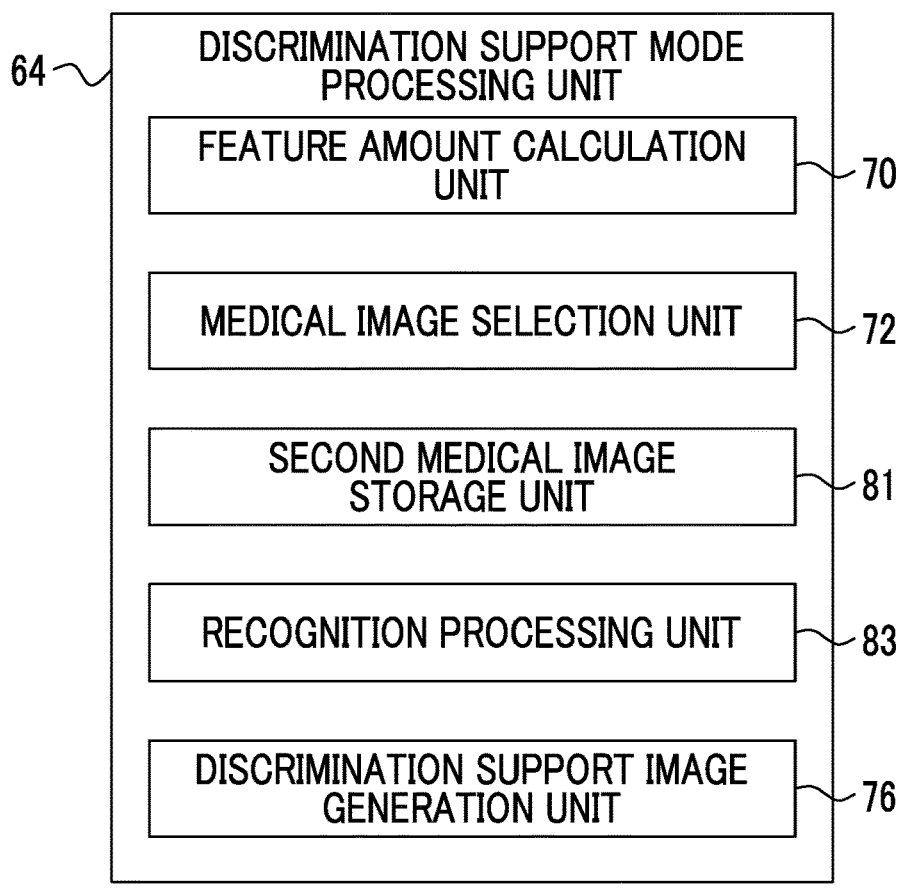
FIG. 10 is a block diagram illustrating the functions of a discrimination support mode processing unit comprising a second medical image storage unit.
Figure 11:
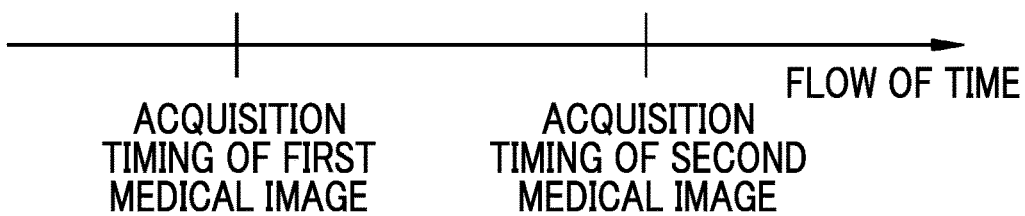
FIG. 11 is an explanatory view illustrating that the acquisition timing of the second medical image is after the acquisition timing of the first medical image.

In this case, as illustrated in FIG. 10, whenever a second medical image is acquired, the second medical image is stored in the second medical image storage unit 81. Then, in a case where switching to the discrimination support mode is performed and the still image acquisition unit 13b is operated to acquire the first medical image, the feature amounts of the second medical images stored in the second medical image storage unit 81 and the first medical image are compared with each other, and the similarities therebetween are calculated. Then, the recognition processing unit 83 performs the recognition processing on a specific medical image of which the similarity of the feature amount satisfies a specific condition, from among the second medical images, and obtains a recognition result. When the recognition result is obtained, the discrimination support image in which a plurality of the specific medical images a plurality of the recognition results are displayed together with the first medical image is displayed on the monitor 18.

Additionally, as illustrated in FIG. 10, an image, which is acquired after the timing when the first medical image is acquired through the same endoscope diagnosis as in the case where the first medical image is acquired, is used as a second medical image. In this case, in the discrimination support mode, no second medical image is present at the timing when the still image acquisition unit 13b is operated to acquire the first medical image. Therefore, the generation and display of the discrimination support image are temporarily made to wait for. In a case where the still image acquisition unit 13b is operated to acquire a second medical image after the acquisition of the first medical image, the acquired second medical image and the first medical image are compared with each other. A discrimination support image is generated on the basis of this comparison, and is displayed on the monitor 18. In addition, which of the images acquired in the discrimination support mode are to be used as the first medical image or the second medical image may be set by the console 19.

Figure 12:
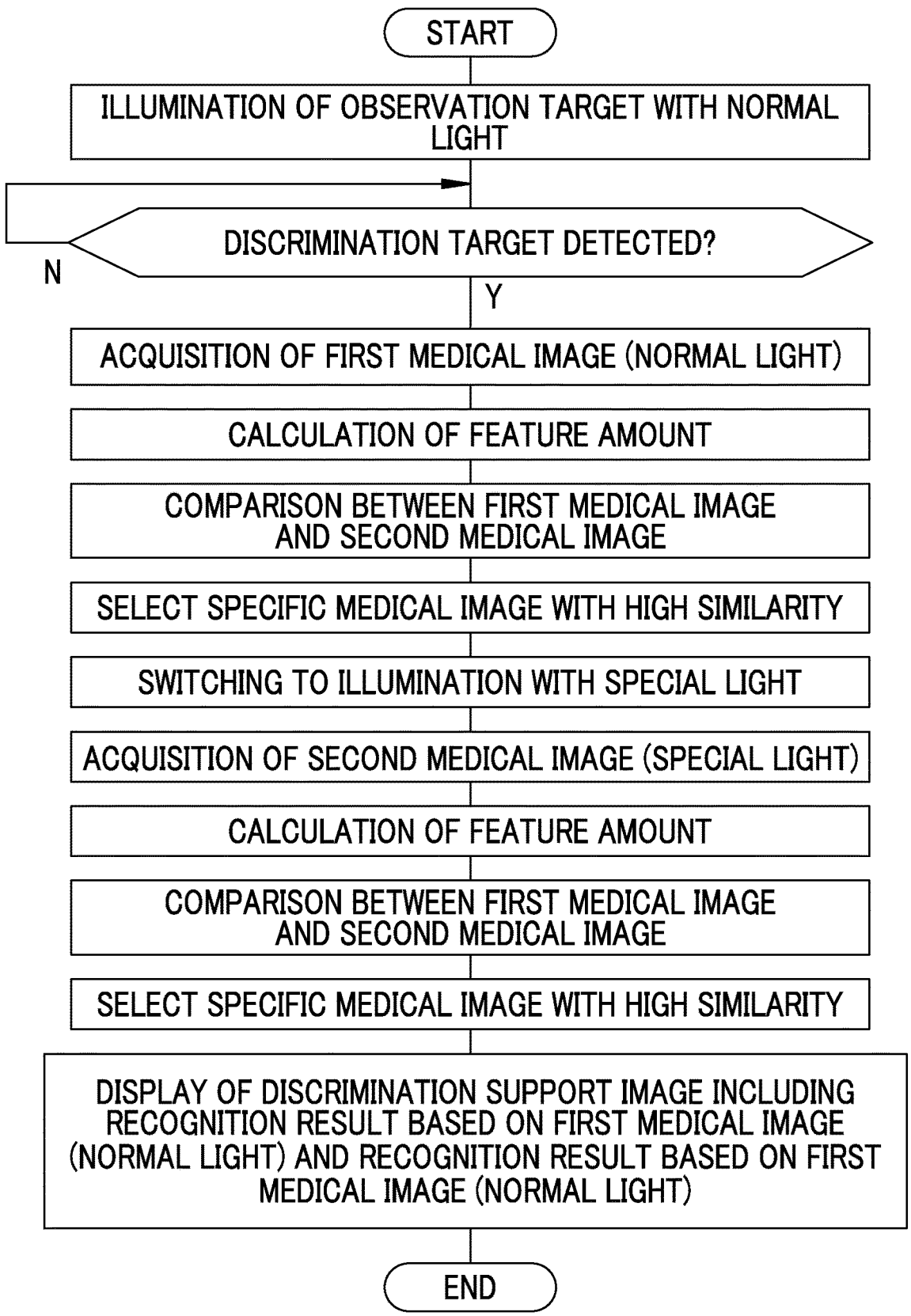
FIG. 12 is a flowchart illustrating a series of flow of the discrimination support mode in a case where the discrimination support mode illumination light is the normal light and special light.

In addition, in the above first and second embodiments, the normal light is used as the discrimination support mode illumination light. However, the special light may be used in addition to this. In this case, in the discrimination support mode, as illustrated in FIG. 12, in a case where the still image acquisition unit 13b is operated, first, the first medical image (normal light) is acquired by imaging the observation target illuminated with the normal light. After the first medical image (normal light) is acquired, as illustrated in the first and second embodiments, the feature amount of the first medical image (normal light) is calculated. Then, a similarity is calculated by performing comparison to the feature amount of the second medical image, and a specific medical image of which the similarity to the first medical image (normal light) satisfies a specific condition is selected out of the second medical images. Additionally, a recognition result of the specific medical image is also acquired together.

Next, in a case where the selection of the specific medical image and the acquisition of the recognition result based on the first medical image (normal light) are completed, the light source control unit 22 controls the light source unit 20 such that the observation target is illuminated with the special light instead of the normal light. Then, the first medical image (special light) is acquired by operating the still image acquisition unit 13b to imaging the observation target illuminated with the special light. After the first medical image (special light) is acquired, as illustrated in the first and second embodiments, the feature amount of the first medical image (special light) is calculated. Then, a similarity is calculated by performing comparison to the feature amount of the second medical image, and a specific medical image of which the similarity to the first medical image (special light) satisfies a specific condition is selected out of the second medical images. Additionally, a recognition result of the specific medical image is also acquired together.

Figure 13:
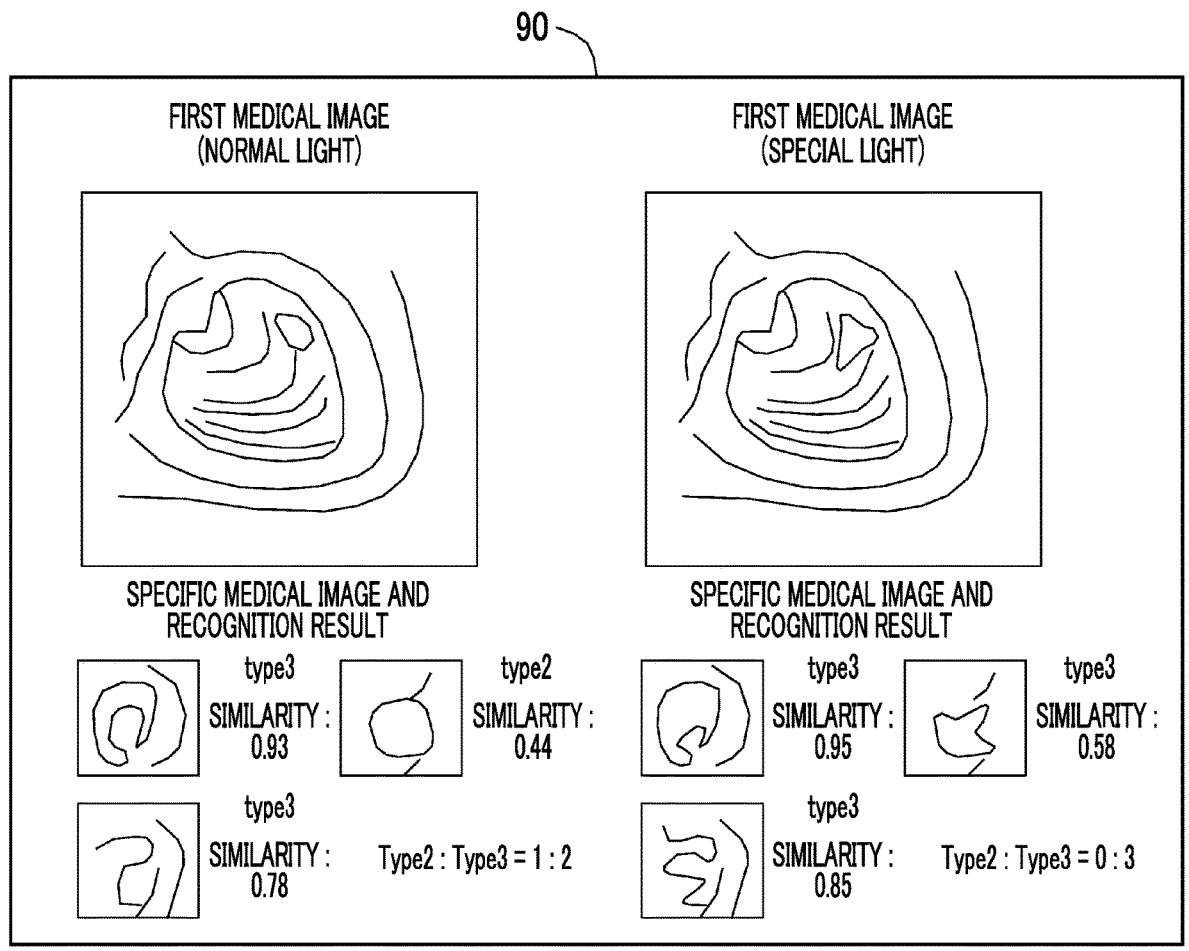
FIG. 13 is an image view illustrating a discrimination support image in a case where the normal light and the special light are used as the discrimination support mode illumination light.

Next, in a case where the selection of the specific medical image and the acquisition of the recognition result based on the first medical image (special light) are completed, a discrimination support image for supporting the discrimination the observation target appearing in the first medical image (normal light) and the observation target appearing in the second medical image (special light) is generated. As illustrated in FIG. 13, in a discrimination support image 90, the first medical image (normal light), and a plurality of specific medical images with high similarities to the first medical image (normal light) are displayed, and recognition results thereof are displayed on the specific medical images, respectively. Additionally, regarding the recognition results, the ratio of kinds is displayed together. Additionally, in parallel with these, the first medical image (special light), and a plurality of specific medical images with high similarities to the first medical image (special light) are displayed, and recognition results thereof are displayed on the specific medical images, respectively.

Here, in the first medical image (special light) obtained by the special light, an observation target that cannot be checked in the first medical image (normal light) obtained by the normal light can be checked. For that reason, even a recognition result that cannot be obtained from the first medical image (normal light) can be obtained from the first medical image (special light). Hence, compared to a case where the observation target is discriminated by providing the recognition results using not only the normal light but also the special light the observation target can be more reliably discriminated. In addition, not only one kind of special light but also a plurality of kinds of special light may be emitted, and recognition results of the recognition processing, may be obtained from a plurality of first medical images (special light) obtained by emitting various kinds of special light.

Figure 14:
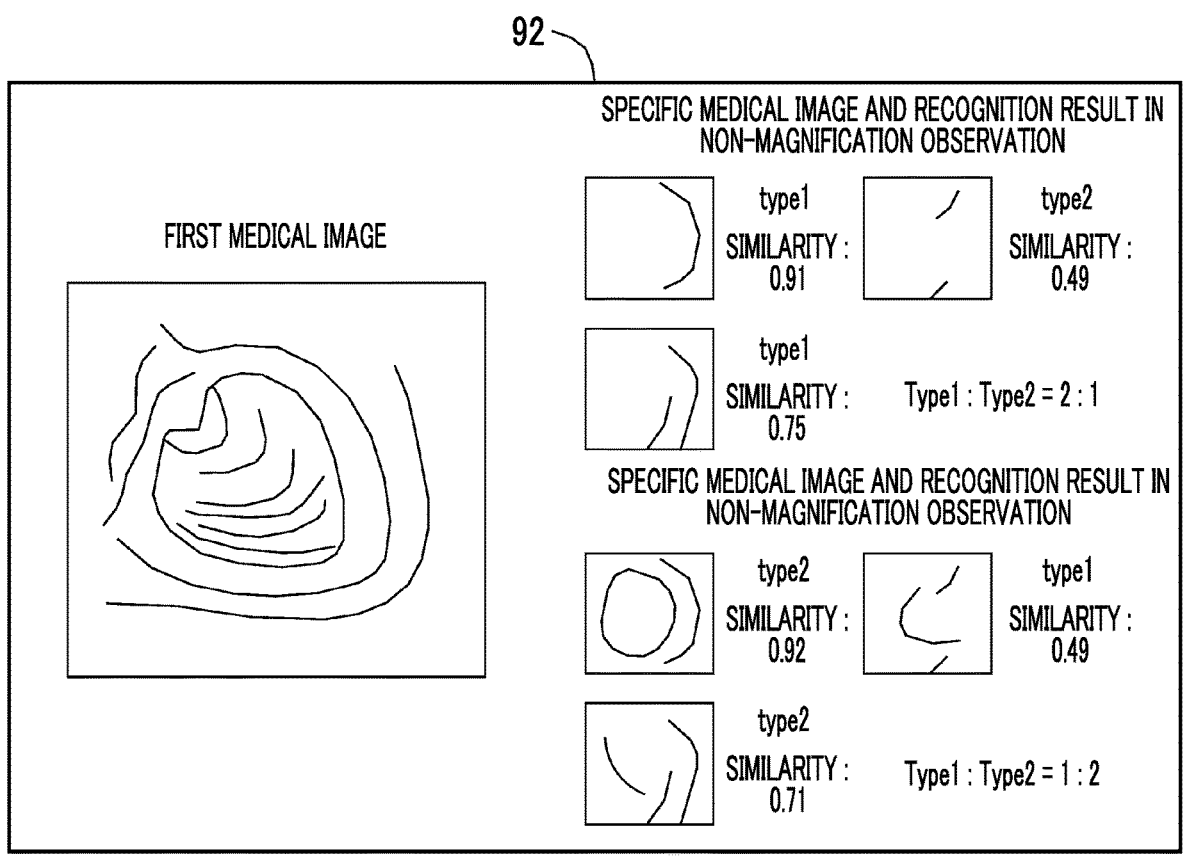
FIG. 14 is an image view illustrating a discrimination support image including a specific medical image and a recognition result thereof during non-magnification observation, and a specific medical image and a recognition result thereof during magnification observation.

In addition, in the above first and second embodiments, a plurality of second medical images having different magnification factors with respect to the same observation target, and recognition results thereof may be used as the second medical images to be compared with the first medical image. This is because the recognition results may vary depending on the magnification factors of the observation target. For example, even in a case where a recognition result of Type 1 is obtained in the case of the non-magnification observation in which the observation target is observed with a first magnification factor, there is a case where a recognition result of Type 2 different from Type 1 is obtained in the case of the magnification observation in which the observation target is observed with a second magnification factor larger than the first magnification factor. Hence, in this case as illustrated in a discrimination support image 92 of FIG. 14, not only the specific medical images obtained in the case of the non-magnification observation and the recognition results thereof but also specific medical images obtained in the case of the magnification observation and recognition results thereof are displayed as the specific medical images with similarities to the first medical image. Accordingly, the discrimination of the observation target can be reliably performed. In addition, although the magnification factor of the observation target can be changed by the zoom lens 36a provided in the magnifying optical system 36, the magnification factor can also be changed by adjusting, the distance between the distal end part 12d of the endoscope and the observation target.

In the above first and second embodiments, the observation target is illuminated the four-color LEDs 20a to 20d. However, the observation target may be illuminated using a laser light source and a fluorescent body. In the following, only portions different from the first and second embodiments will be described, and description of substantially the same portions as those of the first and second embodiments will be omitted.

Figure 15:
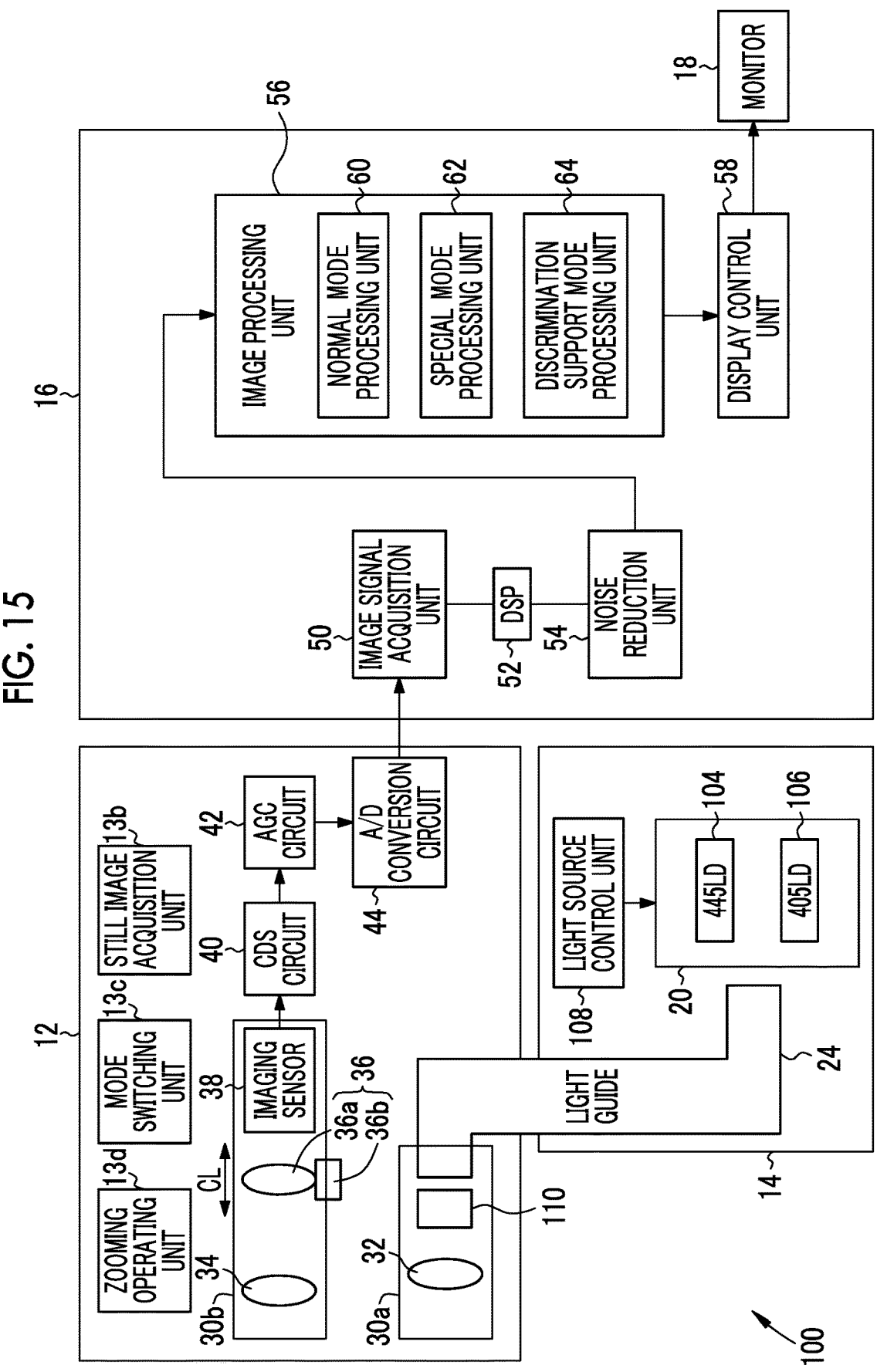
FIG. 15 is a block diagram illustrating the functions of the endoscope system that performs illumination of an observation target using a laser light source and a fluorescent body.

As illustrated in FIG. 15, in the endoscope system 100, in the light source unit 20 of the light source device 14, a blue laser light source that emits blue laser light having a center wavelength of 445±10 nm (written as "445LD"; LD represents Laser Diode) 104 and a blue-violet laser light source (written as "405LD") 106 that emits blue-violet laser light having a center wavelength of 405±10 nm are provided instead of the four-color LEDs 20a to 20d. The light emission from semiconductor light-emitting elements of the respective light sources 104 and 106 are individually controlled by a light source control unit 108, and the quantity-of-light ratio of the emitted light of the blue laser light source 104 and the emitted light of the blue-violet laser light source 106 is changeable.

The light source control unit 108 turns on the blue laser light source 104 in the case of the normal mode or the discrimination support mode. In contrast, in the case of the special mode, both the blue laser light source 104 and the blue-violet laser light source 106 are turned on, and the light emission ratio of the blue laser light is controlled to be larger than the light emission ratio of the blue-violet laser light.

In addition, it is preferable that the half width of the blue laser light or the blue-violet laser light is about ±10 nm. Additionally, as the blue laser light source 104 and the blue-violet laser light source 106, broad area type InGaN-based laser diodes can be utilized, and InGaNAs-based laser diodes and GaNAs-based laser diodes can also be used. Additionally, a configuration using a light emitter, such as a light emitting diode, may be adopted as the above light source.

The illumination optical system 30a is provided with a fluorescent body 110 that the blue laser light or the blue-violet laser light from the light guide 24 enters in addition to the illumination lens 32. The fluorescent body 110 is excited by the blue laser light to emit fluorescence. Additionally, a portion of the blue laser light is transmitted through the fluorescent body 110 without exciting the fluorescent body 110. The blue-violet laser light is transmitted through the fluorescent body 110 without exciting the fluorescent body 110. The inside of the body of the observation target is illuminated with the light emitted from the fluorescent body 110 via the illumination lens 32.

Figure 16:
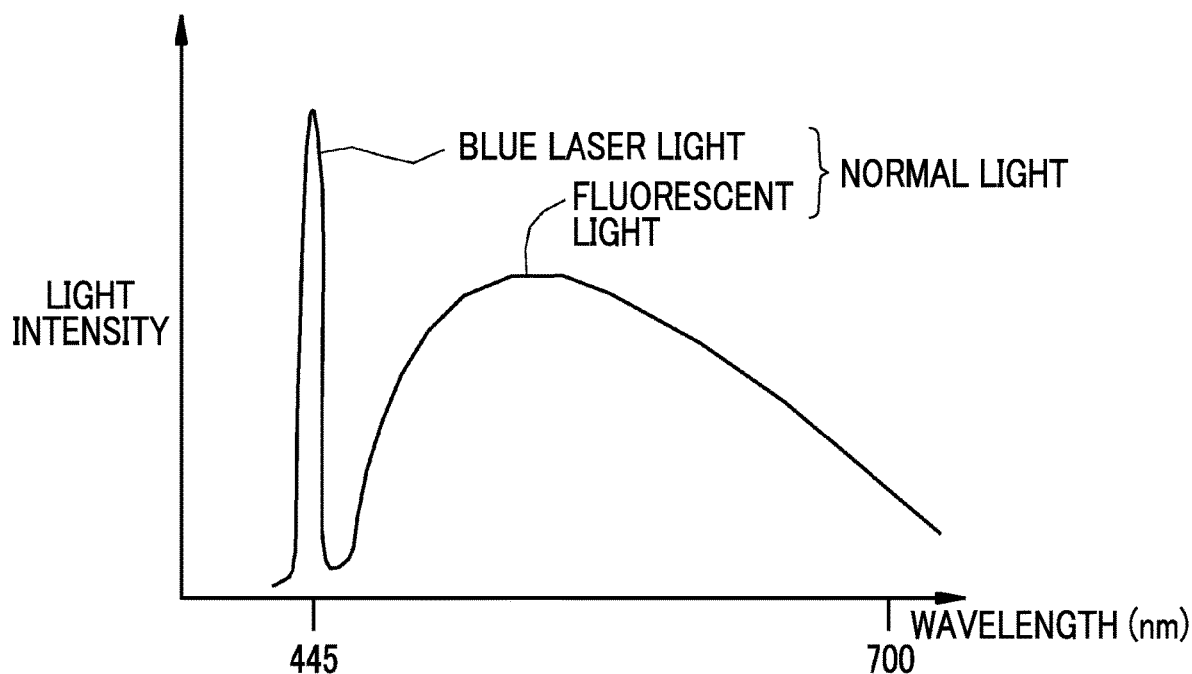
FIG. 16 is a graph illustrating the spectroscopic spectrum of the normal light in the endoscope system that performs the illumination of the observation target using the laser light source and the fluorescent body.

Here, in the normal mode or the discrimination support mode, mainly, the blue laser light enters the fluorescent body 110. Therefore, the broadband light for normal mode, which is obtained by combining the blue laser light with the fluorescence excited and emitted from the fluorescent body 110 due to the blue laser light as illustrated in FIG. 16, is illuminated to the observation target as the normal light. By imaging the observation target illuminated with the normal light by the imaging sensor 38, the normal image including the Bc image signal, the Gc image signal, and the Rc image signal is obtained. Additionally, in the case of the discrimination support mode, the normal image is displayed on the monitor 18, and in a case where the still image acquisition unit 13b is operated, the still image of the normal image is acquired as the first medical image. The discrimination support image is generated and displayed on the basis of the first medical image.

Figure 17:
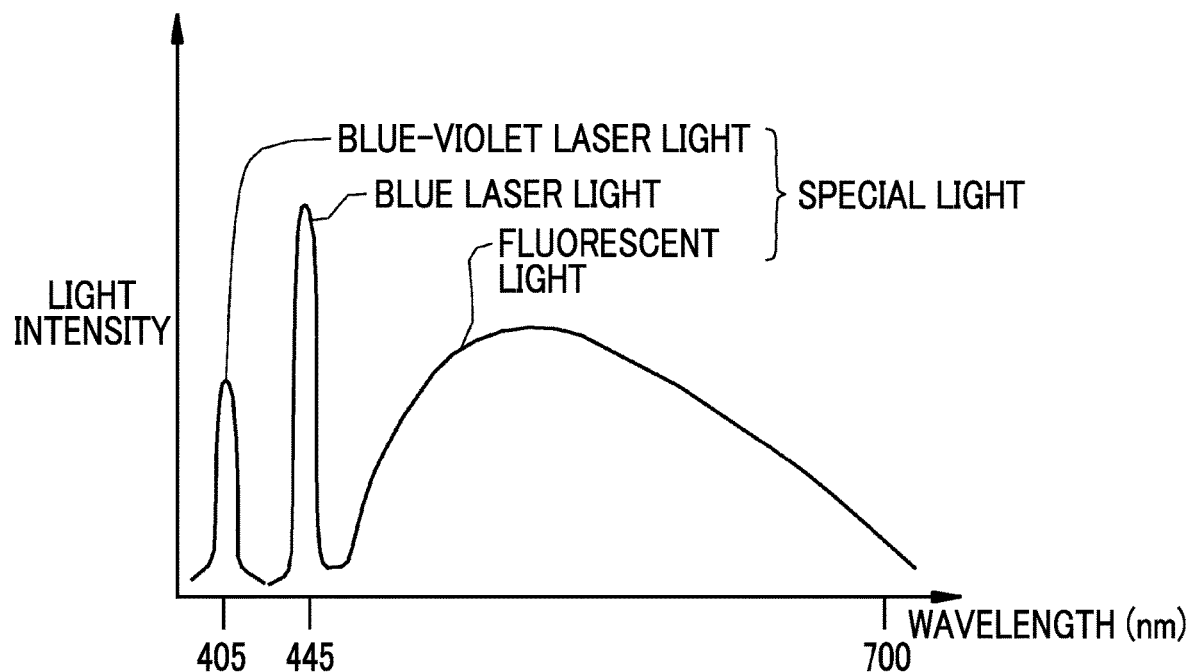
FIG. 17 is a graph illustrating the spectroscopic spectrum of the special light in the endoscope system that performs the illumination of the observation target using the laser light source and the fluorescent body.

On the other hand, in the special mode, the blue-violet laser light and the blue laser light enter the fluorescent body 110. Therefore, the broadband light for special mode, which is obtained by combining the blue-violet laser light, the blue laser light, and the fluorescence excited and emitted from the fluorescent body 110 due to the blue laser light together as illustrated in FIG. 17, is illuminated to the observation target as the special light. By imaging the observation target illuminated with the special light by the imaging sensor 38, the special image including the Bs image signal, the Gs image signal, and the Rs image signal is obtained.

In addition, as the fluorescent body 110, it is preferable to use those configured to include a plurality of types of fluorescent bodies (for example, a YAG-based fluorescent body or fluorescent bodies, such as BAM ($BaMgAl_{10}O_{17}$)) that absorb a portion of the blue laser light and are excited to emit light in green to yellow. As in the present configuration example, in a case where the semiconductor light-emitting elements are used as the excitation light sources of the fluorescent body 110, high-sensitive white light with a high emission ratio can be acquired, the intensity of the white light can be easily adjusted, and changes in color temperature and chromaticity of the white light can be suppressed to be small.

In the above first and second embodiments, the observation target is illuminated the four-color LEDs 20a to 20d. However, the observation target may be illuminated using a white light source, such as a xenon lamp, and a rotation filter. Additionally, the observation target may be imaged by a monochrome imaging sensor instead of the color imaging sensor 38. In the following, only portions different from the first and second embodiments will be described, and description of substantially the same portions as those of the first and second embodiments will be omitted.

Figure 18:
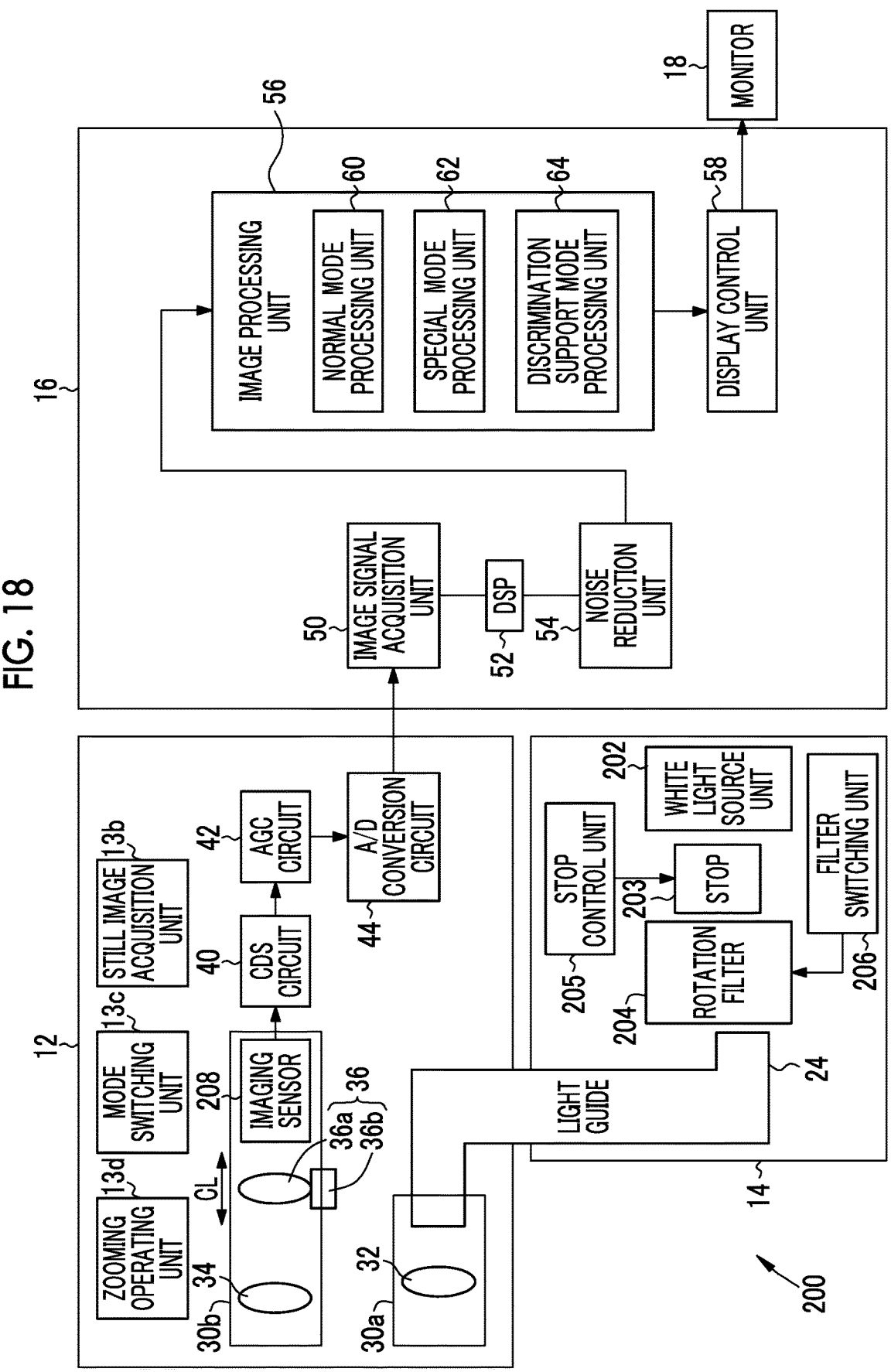
FIG. 18 is a block diagram illustrating the functions of the endoscope system that performs the illumination of the observation target using a white light source and a rotation filter.

In an endoscope system 200 illustrated in FIG. 18, in the light source device 14, a white light source unit 202, a rotation filter 204, and a filter switching unit 206 are provided instead of the respective LEDs 20a to 20d of the endoscope system 10. Additionally, the imaging optical system 30b is provided with a monochrome imaging sensor 208, which is not provided with a color filter, instead of the color imaging sensor 38. Additionally, a stop 203 is provided between the white light source unit 202 and the rotation filter 204, and the area of an opening part of the stop 203 is adjusted by the stop control unit 205.

The white light source unit 202 is a xenon lamp, a white LED, or the like, and emits white light of which the wavelength range ranges from blue to red. The rotation filter 204 comprises an inner filter 210 that is provided on an inner side closest to a rotation axis thereof, an outer filter 212 that is provided outside the inner filter 210, and a discrimination support mode filter 214 (refer to FIG. 19).

The filter switching unit 206 moves the rotation filter 204 in a radial direction. Specifically, the filter switching unit 206 inserts the inner filter 210 into a white light path in a case where the normal mode or the discrimination support mode is set by the mode switching unit 13c. The filter switching unit 206 inserts the outer filter 212 into the white light path in a case where the special mode is set.

Figure 19:
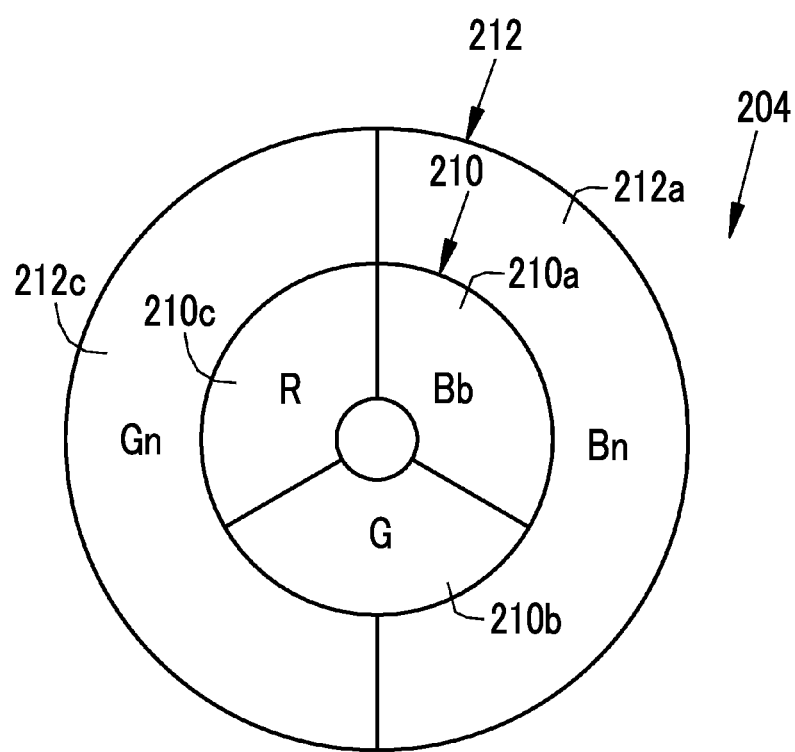
FIG. 19 is a plan view of the rotation filter.

As illustrated in FIG. 19, a Bb filter 210a, a G filter 210b, and an R filter 210c are provided in the circumferential direction in the inner filter 210. The Bb filter 210a transmits the broadband blue light Bb, which has a wavelength range of 400 nm to 500 nm, in the white light. The G filter 210b transmits the green light G in the white light. The R filter 210c transmits the red light R in the white light. Hence, in the normal mode or the discrimination support mode, as the rotation filter 204 rotates, the broadband blue light Bb, the green light G, and the red light R are sequentially radiated toward the observation target as the normal light.

A Bn filter 212a and a Gn filter 212b are provided in the circumferential direction in the outer filter 212. The Bn filter 212a transmits narrowband blue light Bn of 400 nm to 450 nm in the white light. The Gn filter 212b transmits narrowband green light Gn of 530 nm to 570 nm in the white light. Hence, in the special mode, as the rotation filter 204 rotates, the narrowband blue light and the narrowband green light are sequentially radiated toward the observation target as the special light.

In the endoscope system 200, in the normal mode, whenever the observation target is illuminated with the broadband blue light Bb, the given light G, and the red light R, the observation target is imaged by the monochrome imaging sensor 208. As a result, the Bc image signal is obtained at the time of the illumination with the broadband blue light Bb, the Gc image signal is obtained at the time of the illumination with the green light G, and the Re image signal is obtained at the time of the illumination with the red light R. The normal image is constituted of the Bn image signal, the Gc image signal, and the Rc image signal. Additionally, in the discrimination support mode, the normal image is displayed, and in a case where the still image acquisition unit 13b is operated, the still image of the normal image is acquired as the first medical image. The discrimination support image is generated and displayed on the basis of the first medical image.

In the special mode, the observation target is imaged by the monochrome imaging sensor 208 whenever the observation target is illuminated with the narrowband blue light Bn and the narrowband green light Gn. Accordingly, the Bn image signal is obtained at the time of the illumination with the narrowband blue light Bn, and the Gn image signal is obtained at the time of the irradiation with the narrowband green light Gn. The special image is constituted of the Bn image signal and the Gn image signal.

In addition, in the above embodiment, the medical image processor of the embodiment of the invention is applied to the endoscope system that acquires an endoscope image as a medical image. However, it is needless to say that various endoscope systems, such as a capsule endoscope, are applicable. As other medical images, the medical image processor of the embodiment of the invention is applicable to various medical image devices that acquire an X-ray image, a CT image, an MR image, an ultrasound image, a pathological image, a positron emission tomography (PET) image, and the like.

In the above embodiment, the hardware structure of processing units, which execute various kinds of processing, such as the image processing unit 56, are various processors as shown below. The various processors include a central processing unit (CPU) that is a general-purpose processor that executes software (program) to function as various processing units, a programmable logic device (PLD) that is an processor capable of changing circuit configuration after manufacture of a field programmable gate array (FPGA) or the like, an exclusive electric circuit that is an processor that has a circuit configuration that is exclusively designed to execute various kinds of processing.

One processing unit may be constituted of one of these various processors, or may be constituted of two or more same or different processors (for example, a combination of a plurality of the FPGAs or a combination of the CPU and the FPGA). Additionally, the plurality of processing units may be constituted of one processor. As an example in which the plurality of processing units are constituted of the one processor, firstly, as represented by a computer, such as a client or a server, there is a form in which one processor is constituted of a combination of one or more CPUs and software and this processor functions as a plurality of processing units. Secondly, as represented by a system-on-chip (SOC) or the like, there is a form in which a processor, which realizes functions of an overall system including the plurality of processing units with one integrated circuit (IC) chip, is used. In this way, the various processing units are configured by using one or more of the above various processors as the hardware structure(s).

Moreover, the hardware structures of these various processors are more specifically circuitries of a form in which circuit elements, such as semiconductor elements, are combined together.

Explanation of References
10: endoscope system
12: endoscope
12a: insertion part
12b: operating part
12c: bending part
12d: distal end part
13a: angle knob
13b: still image acquisition unit
13c: mode switching unit
13d: zooming operating unit
14: light source device
16: processor device
18: monitor
19: console
20: light source unit
20a: V-LED
20b: B-LED
20c: G-LED
20d: R-LED
22: light source control unit
23: wavelength cutoff filter
24: light guide
30a: illumination optical system
30b: imaging optical system
32: illumination lens
34: objective lens
36: magnifying optical system
36a: zoom lens
36b: lens drive unit
38: imaging sensor
40: CDS circuit
42: AGC circuit
44: A/D conversion circuit
50: image signal acquisition unit
52: DSP
54: noise reduction unit
56: image processing unit
58: display control unit
60: normal mode processing unit
62: special mode processing unit
64: discrimination support mode processing unit
70: feature amount calculation unit
72: medical image selection unit
74: medical image storage unit
76: discrimination support image generation unit
80: first medical image
81: second medical image storage unit
82: medical image
83: recognition processing unit
84: recognition result
86: discrimination support image
88: ratio
90: discrimination support image
92: discrimination support image
100: endoscope system
104: blue laser light source
106: blue-purple laser light source
108: light source control unit
110: fluorescent body
200: endoscope system
202: white light source unit
204: rotation filter
205: stop control unit
206: filter switching unit
208: imaging sensor
210: inner filter
210a: Bb filter
210b: G filter
210c: R filter
212: outer filter
212a: Bn filter
212b: Gn filter

What is claimed is:

1. A medical image processing device comprising:
a processor configured to:
acquire a first normal light medical image obtained by imaging an observation target illuminated by normal light, by an imaging unit including an image sensor, and a first special light medical image obtained by imaging the observation target illuminated by special light whose wavelength is different from the normal light, by the imaging unit;
perform comparison between each of the first normal light medical image and the first special light medical image, and each of a plurality of second medical images to be a comparison target with respect to the first normal light medical image and the first special light medical image, and acquire a plurality of first specific medical images and a plurality of second specific medical images selected in accordance with a result of the comparison from among the plurality of second medical images, the plurality of first specific medical images having similarities above a predetermined threshold to the first normal light medical image, the plurality of second specific medical images having similarities above a predetermined threshold to the first special light medical image; and display the first normal light medical image, the plurality of first specific medical images and recognition results obtained from recognition processing that is performed on the plurality of first specific medical images to recognize the observation target, and display the first special light medical image, the plurality of second specific medical images and recognition results obtained from recognition processing that is performed on the plurality of second specific medical images to recognize the observation target, on a display.

2. The medical image processing device according to claim 1, wherein the processor is further configured to compare a feature amount of the first medical image with a feature amount of each of the plurality of second medical images, and selects the specific medical image in accordance with a similarity between the feature amounts.

3. The medical image processing device according to claim 2, wherein the feature amount is at least any one of a blood vessel density, a blood vessel shape, a blood vessel branch number, a blood vessel thickness, a blood vessel length, a blood vessel meandering degree, a blood vessel invasion degree, a gland duct shape, a gland duct opening shape, a gland duct length, a gland duct meandering degree, or color information, or a value obtained by combining two or more thereof.

4. The medical image processing device according to claim 1, wherein a plurality of kinds of the recognition results are present, and the processor is further configured to display a ratio of the recognition results for each kind on the display.

5. The medical image processing device according to claim 1, wherein a plurality of kinds of the recognition results are present, and the processor is further configured to display the number of the recognition results on the display for each kind.

6. The medical image processing device according to claim 1, wherein the processor is further configured to display a user recognition result, which is recorded in association with each of the plurality of second medical images and is obtained by determining the observation target by a user, on the display.

7. The medical image processing device according to claim 1, wherein the recognition results include a recognition result, which is recorded in association with each of the plurality of second medical images and is obtained by performing recognition processing in another medical image processing device.

8. The medical image processing device according to claim 1, wherein the recognition results include at least the observation target being a lesioned part and the observation target being a normal part.

9. The medical image processing device according to claim 1, wherein the recognition results include at least the kind of lesion.

10. The medical image processing device according to claim 1, wherein each of the plurality of second medical images is registered in advance in a medical image storage.

11. The medical image processing device according to claim 1, wherein each of the plurality of second medical images is obtained by imaging with the imaging unit at a timing before the first medical image.

12. The medical image processing device according to claim 1, wherein each of the plurality of second medical images is obtained by imaging with the imaging unit at a timing after the first medical image.

13. The medical image processing device according to claim 1, wherein the special light has a wavelength range of 450 nm or less.

14. An endoscope system comprising:

a light source device that generates illumination light for illuminating an observation target;

an endoscope that has an imaging unit including an image sensor that images the observation target illuminated with the illumination light;

a processor configured to:

acquire a first normal light medical image obtained by imaging the observation target illuminated by normal light, by the imaging unit, and a first special light medical image obtained by imaging the observation target illuminated by special light whose wavelength is different from the normal light, by the imaging unit:

perform comparison between each of the first normal light medical image and the first special light medical image, and each of a plurality of second medical images to be a comparison target with respect to the first normal light medical image and the first special light medical image, and acquire a plurality of first specific medical images and a plurality of second specific medical images selected in accordance with a result of the comparison from among the plurality of second medical images, the plurality of first specific medical images having similarities above a predetermined threshold to the first normal light medical image, the plurality of second specific medical images having similarities above a predetermined threshold to the first special light medical image; and display the first normal light medical image, the plurality of first specific medical images and recognition results obtained from recognition processing that is performed on the plurality of first specific medical images to recognize the observation target, and display the first special light medical image, the plurality of second specific medical images and recognition results obtained from recognition processing that is performed on the plurality of second specific medical images to recognize the observation target, on a display.

15. A method of operating a medical image processing device comprising:

a medical image acquisition step of acquiring a first normal light medical image, which is obtained by imaging an observation target illuminated by normal light, by an imaging unit including an image sensor, and a first special light medical image obtained by imaging the observation target illuminated by special light whose wavelength is different from the normal light, by the imaging unit;

a medical image selection step of performing comparison between each of the first normal light medical image and the first special light medical image, and each of a plurality of second medical images to be a comparison target with respect to the first normal light medical image and the first special light medical image, and acquiring a plurality of first specific medical images and a plurality of second specific medical images selected in accordance with a result of the comparison from among the plurality of second medical images, the plurality of first specific medical images having similarities above a predetermined threshold to the first normal light medical image, the plurality of second specific medical images having similarities above a predetermined threshold to the first special light medical image; and a display step of displaying the first normal light medical image, the plurality of first specific medical images and recognition results obtained from recognition processing that is performed on the plurality of first specific medical images to recognize the observation target, and display the first special light medical image, the plurality of second specific medical images and recognition results obtained from recognition processing that is performed on the plurality of second specific medical images to recognize the observation target, on a display.

16. A medical image processing device comprising:

a processor configured to:

acquire a first magnified medical image with a first magnification factor obtained by imaging an observation target with the first magnification factor by an imaging unit including an image sensor, and a second magnified medical image with a second magnification factor obtained by imaging the observation target with the second magnification factor larger than the first magnification factor, by the imaging unit;

perform comparison between each of the first magnified medical image and the second magnified medical image, and each of a plurality of second medical images to be a comparison target with respect to the first magnified medical image and the second magnified medical image, and acquire a plurality of first specific medical images and a plurality of second specific medical images selected in accordance with a result of the comparison from among the plurality of second medical images, the plurality of first specific medical images having similarities above a predetermined threshold to the first magnified medical image, the plurality of second specific medical images having similarities above a predetermined threshold to the second magnified medical image; and display the first magnified medical image, the plurality of first specific medical images and recognition results obtained from recognition processing that is performed on the plurality of first specific medical images to recognize the observation target, and display the second magnified medical image, the plurality of second specific medical images and recognition results obtained from recognition processing that is performed on the plurality of second specific medical images to recognize the observation target, on a display.

* * * * *